(12) United States Patent
Su et al.

(10) Patent No.: US 8,278,055 B2
(45) Date of Patent: Oct. 2, 2012

(54) METHODS AND DEVICE FOR ANALYTE CHARACTERIZATION

(75) Inventors: Xing Su, Cupertino, CA (US); Andrew A. Berlin, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 2159 days.

(21) Appl. No.: 10/697,682

(22) Filed: Oct. 29, 2003

(65) Prior Publication Data

US 2005/0282229 A1  Dec. 22, 2005

Related U.S. Application Data

(63) Continuation-in-part of application No. 10/138,157, filed on May 1, 2002.

(51) Int. Cl.
*G01N 33/53* (2006.01)
*C12Q 1/68* (2006.01)

(52) U.S. Cl. .............. 435/7.1; 436/518; 702/19

(58) Field of Classification Search .......... None
See application file for complete search history.

(56) References Cited

U.S. PATENT DOCUMENTS

| | | | |
|---|---|---|---|
| 4,962,037 A | 10/1990 | Jett et al. | |
| 5,306,403 A | 4/1994 | Vo-Dinh | |
| 5,324,637 A * | 6/1994 | Thompson et al. | 435/68.1 |
| 5,332,666 A | 7/1994 | Prober et al. | |
| 5,405,747 A | 4/1995 | Jett et al. | |
| 5,436,130 A | 7/1995 | Mathies et al. | |
| 5,721,102 A | 2/1998 | Vo-Dinh | |
| 5,776,674 A | 7/1998 | Ulmer | |
| 5,783,389 A | 7/1998 | Vo-Dinh | |
| 5,814,516 A | 9/1998 | Vo-Dinh | |
| 5,821,058 A | 10/1998 | Smith et al. | |
| 5,866,336 A | 2/1999 | Nazarenko et al. | |
| 6,002,471 A | 12/1999 | Quake | |
| 6,146,227 A | 11/2000 | Mancevski | |
| 6,174,677 B1 | 1/2001 | Vo-Dinh | |
| 6,210,896 B1 | 4/2001 | Chan | |
| 6,355,420 B1 | 3/2002 | Chan | |
| 6,514,767 B1 | 2/2003 | Natan | 436/166 |
| 7,005,264 B2 * | 2/2006 | Su et al. | 435/6 |
| 2003/0059822 A1 | 3/2003 | Chan et al. | |
| 2003/0207326 A1 | 11/2003 | Su et al. | |

FOREIGN PATENT DOCUMENTS

| | | |
|---|---|---|
| WO | WO/01/25794 | 4/2001 |
| WO | WO/03/078649 | 9/2003 |
| WO | WO/03/106620 | 12/2003 |

OTHER PUBLICATIONS

Branton et al (Branton Lab), Nanopore Technology, Probing Polynucleotides with a Nanopore: High Speed, Single Moleudle DNA Sequencing, Nanopore Sequencing Description, 3 pages, dated Feb. 3, 2002.*
Doering, et al., "Spectroscopic Tags Using Dye-Embedded Nanoparticles and Surface—Enhanced Raman Scattering", *Analytical Chemistry*, :5-9, 2003.
Fisher, et al, "Lipid Binding—Induced Conformational Changes in the N-Terminal Domain of Human Apolipoprotein E", *J. of Lipid Res.*, 40(1):93-99 (Jan. 1999).
Lillo, et al., "Design and Characterization of a Multisite Fluorescence Energy-Transfer System for Protein Folding Studies: A Steady-State and Time-Resolved Study of Yeast Phosphoglycerate kinase", *Biochem. Am. Chem. Soc.* 36(37):11261-11272 (1997).
Mulvaney, et al., "Glass-Coated, Analyte-Tagged Nanoparticles: A New Tagging System Based on Detection with Surface-Enhanced Raman Scattering", *Am Chem Soc.* 19:4784-4790 (2003).

* cited by examiner

*Primary Examiner* — Julie Ha
(74) *Attorney, Agent, or Firm* — Pillsbury Winthrop Shaw Pittman LLP

(57) ABSTRACT

The methods and apparatus, disclosed herein are of use for sequencing and/or identifying proteins, polypeptides and/or peptides. Proteins containing labeled amino acid residues may be synthesized and passed through nanopores. A detector operably coupled to a nanopore may detect labeled amino acid residues as they pass through the nanopore. Distance maps for each type of labeled amino acid residue may be compiled. The distance maps may be used to sequence and/or identify the protein. Apparatus of use for protein sequencing and/or identification is also disclosed herein. In alternative methods, other types of analytes may be analyzed by the same techniques.

19 Claims, 21 Drawing Sheets

Tagging Lysine, Arginine and N-terminal Residues

1) Label with thiol group – Maleimide activation

2) Label with carboxyl group – EDAC activation

Tagging Serine, Threonine and Glycosylated Residues

1) Label with amino oligo – sugar oxidation

2) Label with amino oligo – Ser/Thr oxidation

METHODS AND DEVICE FOR ANALYTE CHARACTERIZATION

RELATED APPLICATIONS

The present application is a continuation-in-part of U.S. patent application Ser. No. 10/138,157, filed on May 1, 2002.

BACKGROUND

1. Field

The disclosed methods and apparatus relate to the analysis of analytes including, but not limited to, proteins, polypeptides, peptides, lipids and polysaccharides. In particular, the methods and apparatus relates to protein, polypeptide and/or peptide identification and/or sequencing.

2. Related Art

Identification and/or sequencing of analytes, such as proteins, are critical for medical diagnostics, forensics, toxicology, pathology, biological warfare, public health and numerous other fields. The ability to identify a particular pathogen or agent may depend on identification of one or more specific analytes characteristic of that pathogen or agent. Identification of regulatory pathways involved in disease processes, metabolism, growth and cell division may depend on identification and/or sequencing of analytes. Although a great deal of research is presently directed towards identification and/or sequencing of nucleic acids or proteins, other analytes such as carbohydrates, polysaccharides, lipids, fatty acids, etc. may be of importance. The methods and apparatus disclosed herein are focused on identification and/or sequencing of proteins, polypeptides and peptides. However, they are also of use for analysis of other types of analytes.

Existing methods for protein sequencing, based on the Edman degradation technique, are limited by the length of the protein that can be sequenced. Accurate sequence determination is limited to about 50 to 100 amino acid residues per sequencing run. Sequencing of longer proteins, which may be thousands of amino acid residues in length, requires cleavage into smaller fragments and assembly of overlapping short sequences. The process is laborious, expensive, inefficient and time-consuming and typically requires the use of radioactive labels and other hazardous chemicals, which can pose safety and waste disposal problems.

A variety of techniques are available for identification of proteins, polypeptides and peptides. Commonly, these involve binding and detection of antibodies that can recognize one or more epitopic domains on the protein. Although antibody-based identification of proteins is fairly rapid, such assays may occasionally show unacceptably high levels of false positive or false negative results, due to cross-reactivity of the antibody with different antigens, low antigenicity of the target analyte (leading to low sensitivity of the assay), non-specific binding of antibody to various surfaces, etc. They also require the preparation of antibodies that can recognize an individual protein or peptide. As such, they are not suitable for the identification of novel proteins that have not previously been characterized. More recently, mass spectroscopy has been used for peptide identification and/or sequencing. Proteins and polypeptides may be cleaved into smaller fragments and the amino acid composition of the fragments may be identified by mass spectroscopy. Analysis of a sufficient number of overlapping fragments can provide data on amino acid sequence. This process is also laborious, expensive and requires substantial purification of the protein or peptide to be analyzed.

A need exists in the art for methods and apparatus suitable for the identification and/or sequencing of analytes, including proteins and peptides that have not previously been identified or characterized.

BRIEF DESCRIPTION OF THE DRAWINGS

The following drawings form part of the specification and are included to further demonstrate certain aspects of the disclosed methods and apparatus. The methods and apparatus may be better understood by reference to one or more of these drawings in combination with the detailed description presented herein.

DETAILED DESCRIPTION

Definitions

Figure 1:
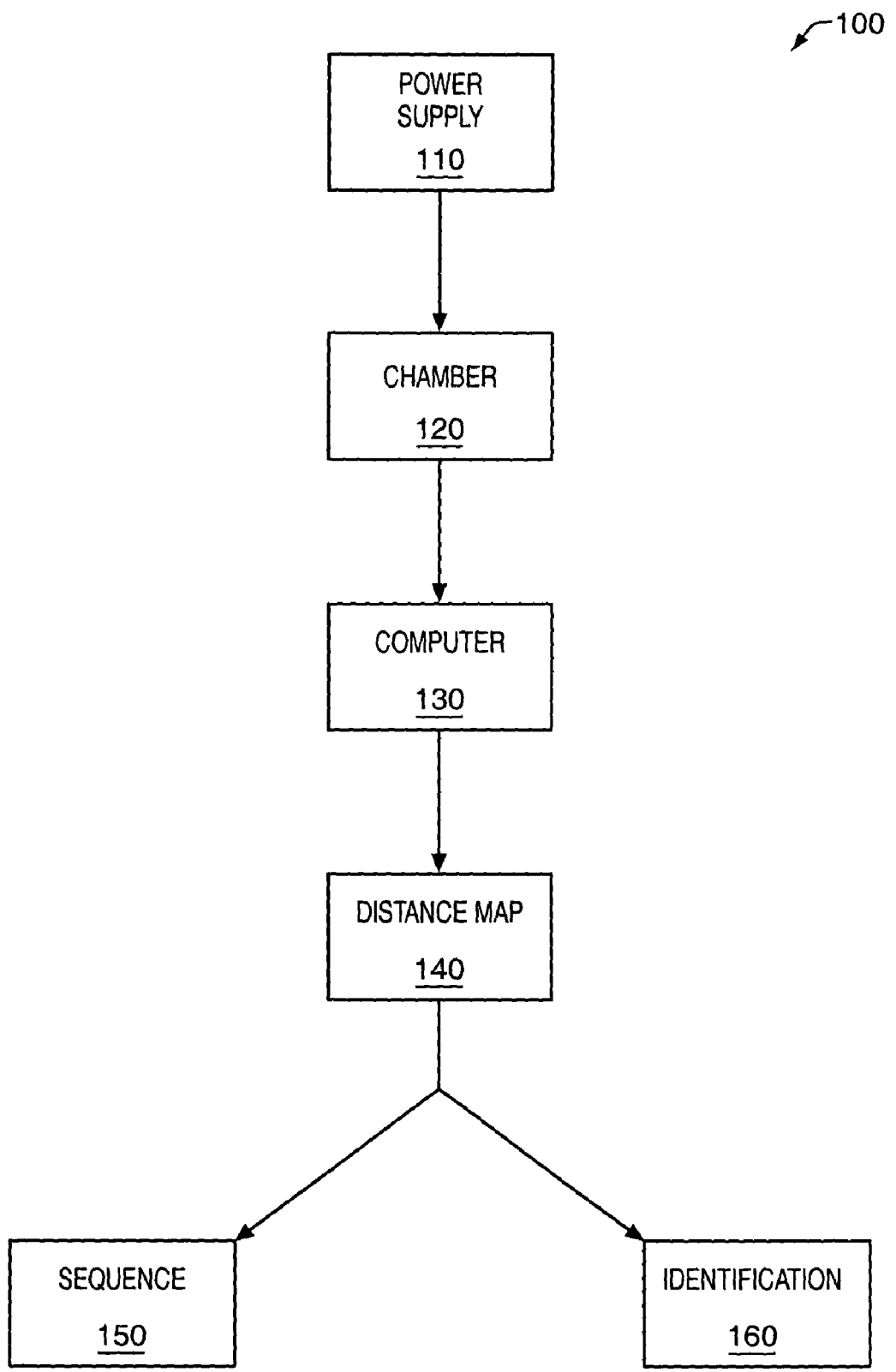
FIG. 1 is a flow chart illustrating a non-limiting exemplary apparatus 100 (not to scale) and methods for protein sequencing 150 and/or identification 160 by generation of distance maps 140.

As used herein, "a" or "an" may mean one or more than one of an item.

The terms "protein," "polypeptide" and "peptide" refer to polymeric molecules assembled in linear fashion from amino acids. The distinction between the terms is primarily one of length, with peptides typically ranging from about 2 to about 25 amino acid residues, polypeptides from about 10 to about 100 amino acid residues and proteins about 50 residues or longer. The terms overlap and the skilled artisan will realize that where the following disclosure refers to proteins or polypeptides or peptides, the terms encompass polymers of any length. Where the present specification uses the term "protein", it will be understood that the term also encompasses "polypeptide" and/or "peptide". It is contemplated that proteins to be analyzed may comprise naturally occurring amino acid residues, modified amino acid residues, derivatized amino acid residues, amino acid analogues and/or non-naturally occurring amino acids. Amino acid residues that have been labeled with any labels are also encompassed. Although amino acid residues in naturally occurring proteins are typically joined together by peptide bonds, within the scope of the disclosed methods amino acid residues may be joined by peptide bonds or by any other type of known covalent attachment.

The terms "nanopore", "nanochannel" and "nanotube" refer respectively to a hole, channel or tube with a diameter or width of between 1 and 999 nanometers (nm), more typically between 1 and 100 nm, even more typically between 1 and 10 nm. As used herein, the terms "nanopore", "nanotube" and "nanochannel" may be used interchangeably. The skilled artisan will realize that where the specification refers to a "nanopore," different alternatives may use a "nanochannel" or "nanotube." The only requirement is that the nanopore, nanochannel or nanotube connect one fluid filled compartment to another and allow the passage and detection of labeled proteins.

As used herein, "operably coupled" means that there is a functional and/or structural relationship between two or more units. For example, a detector may be "operably coupled" to a nanopore if the detector is arranged so that it may identify labeled amino acid residues passing through the nanopore. Similarly, a nanopore may be operably coupled to a chamber if proteins in the chamber can pass through the nanopore. A detector may also be "operably coupled" to a nanopore where the detector and/or sensing elements of the detector are integrated into the nanopore.

As used herein, "fluid communication" refers to a functional connection between two or more compartments that allows fluids to pass between the compartments. For example, a first compartment is in "fluid communication" with a second compartment if fluid may pass from the first compartment to the second and/or from the second compartment to the first compartment.

Description of Illustrative Embodiments

The disclosed methods and apparatus are of use for the rapid, automated sequencing and/or identification of proteins. Advantages over prior art methods include high throughput, sensitive detection of single labeled protein molecules, nanometer scale resolution of amino acid residue distances and lower unit cost of protein sequencing and/or identification.

The following detailed description contains numerous specific details in order to provide a more thorough understanding of the claimed methods and apparatus. However, it will be apparent to those skilled in the art that the methods and apparatus may be practiced without these specific details. In other instances, devices, methods, procedures, and individual components that are well known in the art have not been described in detail herein.

As illustrated in FIG. 1, a nucleic acid template may be placed in one or more chambers 120, each chamber 120 to contain a different labeled amino acid. Labeled proteins encoded by the nucleic acid template may be produced by in vitro translation or by linked transcription/translation. The labeled proteins may pass through one or more nanopores associated with each chamber, the nanopores permeating one or more sensor layers operably coupled to a detector. As a labeled protein passes through a nanopore, labeled amino acid residues are detected. The distances between labeled amino acid residues are determined and a distance map 140 is compiled for each type of labeled amino acid residue. The distance maps 140 may be used to sequence 150 and/or identify 160 the labeled protein.

The skilled artisan will realize that the distance maps 140 of consideration may show distances in the sub-nanometer or greater scale. For example, a single amino acid in a linear protein sequence would have a size of about 0.6 nm. During typical gel electrophoresis of proteins (field strength of about 10 volt/cm), molecules may travel about 100 mm in 60 minutes (or about 28,000 nm per second). Since currently available electrical detectors are capable of counting down to the femto second scale, detection of adjacent amino acids is well within the detection limits. Given the mobility rate of proteins under electrophoresis, a 1 nanosecond time frame would be equivalent to a distance of 0.036 nm, which is less than the carbon-carbon bond length of about 0.154 nm. It would take about 20 nanoseconds to detect two adjacent amino acid residues. The distance maps 140 may range from the average subunit distance (0.6 nm) up to the length of a full-length protein, which may be thousands of amino acids long.

In alternative methods, labeled proteins may be prepared by incubating cells in, for example, a solution comprising labeled amino acid and purifying one or more proteins from the incubated cells. In other alternative, cells may be transformed with an expression vector encoding a protein of interest and allowed to form labeled proteins. Where twenty chambers 120 are used containing all twenty different labeled amino acid residues, the distance maps 140 may be compiled into a complete protein sequence 150.

Proteins, Polypeptides and Peptides

Proteins to be analyzed may be: [1] purified from natural sources; [2] expressed by in vitro translation of an mRNA species or by linked transcription/translation of a DNA species; and/or [3] expressed in a host cell that has been transformed with a gene or a complementary DNA (cDNA) species. These methods are not limiting and proteins to be analyzed may be prepared by any method known in the art.

Protein Purification

Proteins to be analyzed may be partially or fully purified from a variety of sources before analysis. Protein purification techniques are well known in the art. These techniques typically involve an initial crude fractionation of cell or tissue homogenates and/or extracts into protein and non-protein fractions. Fractionation may utilize, for example, differential solubility in aqueous solutions, detergents and/or organic solvents, elimination of classes of contaminants such as nucleic acids by enzymatic digestion, precipitation of proteins with ammonium sulphate, polyethylene glycol, antibodies, heat denaturation and the like, followed by ultracentrifugation. A variety of detergents of use in protein purification are known in the art, including but not limited to ionic surfactants (e.g., sodium dodecyl sulphate, sodium cholate, sodium deoxycholate, hexadecyltrimethylammonium bromide) and non-ionic surfactants (e.g., Triton X-100, Tween-20, Brij-35, digitonin, Nonidet® P40, octylglucoside). Non-ionic detergents may be of greater use where electrical detection of tagged residues is used. For optical detection, either ionic or non-ionic detergents may be of use. A detergent that does not exhibit substantial absorption and/or emission at the wavelengths used for excitation and detection would be of greater use for optical detection. Reducing agents such as dithiothreitol or β-mercaptoethanol may be of use to reduce disulfide bonds and dissociate protein aggregates. Low molecular weight contaminants may be removed by dialysis, filtration and/or organic phase extraction.

Protein(s) of interest may be purified using chromatographic and/or electrophoretic techniques to achieve partial or complete purification. Methods suited to the purification of proteins, polypeptides and peptides include, but are not limited to, ion-exchange chromatography, gel exclusion chromatography, polyacrylamide gel electrophoresis, affinity chromatography, immunoaffinity chromatography, hydroxylapatite chromatography, hydrophobic interaction chromatography, reverse phase chromatography, isoelectric focusing, fast protein liquid chromatography (FPLC) and high pressure liquid chromatography (HPLC). These and other methods of protein purification are known in the art and are not limiting for the claimed subject matter. Any known method of protein purification may be used. There is no requirement that the protein must be in its most purified state. Methods exhibiting a lower degree of relative purification may, for example, have advantages in increased recovery of labeled protein.

Affinity chromatography may be used for purification of some proteins. The method relies on an affinity between a protein and a molecule to which it can specifically bind. Chromatography material may be prepared by covalently attaching a protein-binding ligand, such as an antibody, antibody fragment, receptor protein, substrate, inhibitor, product or an analog of such ligands to an insoluble matrix, such as column chromatography beads or a nylon or other membrane. The matrix may then be used to specifically adsorb the target protein from a solution. Elution occurs by changing the solvent conditions (e.g. pH, ionic strength, temperature, detergent concentration, etc.). One of the most common forms of affinity chromatography is immunoaffinity chromatography. Methods for generating antibodies against various types of proteins for use in immunoaffinity chromatography are well known in the art.

Proteins of interest may be specifically labeled in order to facilitate purification. The protein of interest may be followed through a purification protocol by looking for the presence of the label. Proteins may be post-translationally labeled using side chain specific and/or selective reagents as discussed below. Various methods for protein labeling are known in the art, discussed in more detail below.

In Vitro Translation

Proteins may be expressed using an in vitro translation system with mRNA templates. Complete kits for performing in vitro translation are available from commercial sources, such as Ambion (Austin, Tex.), Promega (Madison, Wis.), Amersham Pharmacia Biotech (Piscataway, N.J.), Invitrogen (Carlsbad, Calif.) and Novagen (Madison, Wis.). Such kits may utilize total RNA, purified polyadenylated mRNA, and/or purified individual mRNA species obtained from a cell, tissue or other sample. Methods of preparing different RNA fractions and/or individual mRNA species for use in in vitro translation are known. (E.g., Sambrook, et al., Molecular Cloning: A Laboratory Manual, Cold Spring Harbor Laboratory Press, Cold Spring Harbor, N.Y., 1989; Ausubel et al., Current Protocols in Molecular Biology, Wiley and Sons, New York, N.Y., 1994).

Commonly used in vitro translation systems are based on rabbit reticulocyte lysates, wheat germ extracts and E. coli extracts. In vitro translation systems based on rabbit reticulocyte lysates are particularly robust and efficient for eukaryotic translation. The systems contain crude cell extracts including ribosomal subunits, transfer RNAs (tRNAs), aminoacyl-tRNA synthetases, initiation, elongation and termination factors and/or all other components required for translation. The natural amino acids present in such extracts may be supplemented with one or more different types of labeled amino acids. Depending on the application, the label may be restricted to a single type of amino acid. Alternatively, a sample to be translated may be divided up into different sub-samples, each of which may be exposed to a different type of labeled amino acid. For optical detection methods, tryptophan or 5-fluoro-tryptophan exhibit natural fluorescence and may be used for Raman spectroscopy. Labels may be added to other amino acid residues either before protein synthesis or by post-translational modification. Other components of use in supplementing in vitro translation systems and methods of use of such systems are known in the art (see, e.g., Ambion website).

In vitro translation may be linked to transcription of genes to generate mRNAs. Such linked transcription/translation systems may use PCR® amplification products and/or DNA sequences inserted into standard expression vectors such as BACs (bacterial artificial chromosomes), YACs (yeast artificial chromosomes), cosmids, plasmids, phage and/or other known expression vectors. Linked transcription/translation systems are available from commercial sources (e.g., Proteinscript™ II kit, Ambion, Austin, Tex.; Quick Coupled System, Promega, Madison, Wis.; Expressway, Invitrogen, Carlsbad, Calif.). Such systems may incorporate various elements to optimize the efficiency of transcription and translation, such as polyadenylation sequences, consensus ribosomal binding (Kozak) sequences, Shine-Dalgarno sequences and/or other regulatory sequences known in the art.

Labeled proteins may be purified from the crude in vitro translation mixture prior to analysis, or alternatively may be analyzed without purification. The use of protein purification may depend in part on whether a crude RNA fraction or a purified RNA species is used as the template for translation.

Protein Expression in Host Cells

Nucleic acids encoding target proteins of interest may be incorporated into expression vectors for transformation into host cells and production of the encoded proteins. Non-limiting examples of host cell lines known in the art include bacteria such as E. coli, yeast such as Pichia pastoris, and mammalian cell lines such as VERO cells, HeLa cells, Chinese hamster ovary cell lines, human embryonic kidney (HEK) 293 cells, mouse neuroblastoma N2A cells, or the W138, BHK, COS-1, COS-7, 293, HepG2, 3T3, RIN, L-929 and MDCK cell lines. These and other host cell lines may be obtained from standard sources, such as the American Type Culture Collection (Rockville, Md.) or commercial vendors.

A complete gene can be expressed or fragments of a gene encoding portions of a protein can be expressed. The gene or gene fragment encoding protein(s) of interest may be inserted into an expression vector by standard cloning techniques. Expression libraries containing part or all of the messenger RNAs expressed in a given cell or tissue type may be prepared by known techniques. Such libraries may be screened for clones encoding particular proteins of interest, for example using antibody or oligonucleotide probes and known screening techniques.

The engineering of DNA segment(s) for expression in a prokaryotic or eukaryotic system may be performed by techniques generally known in the art. Any known expression system may be employed for protein expression. Expression vectors may comprise various known regulatory elements for protein expression, such as promoters, enhancers, ribosome binding sites, termination sequences, polyadenylation sites, etc.

Promoters commonly used in bacterial expression vectors include the β-lactamase, lactose and tryptophan promoter systems. Suitable promoter sequences in yeast expression vectors include the promoters for 3-phosphoglycerate kinase or other glycolytic enzymes. Promoters of use for mammalian cell expression may be derived from the genome of mammalian cells (e.g., metallothionein promoter) or from mammalian viruses (e.g., the adenovirus late promoter or the early and late promoters of SV40). Many other promoters are known and may be used in the practice of the disclosed methods.

Eukaryotic expression systems of use include, but are not limited to, insect cell systems infected with, for example, recombinant baculovirus, or plant cell systems infected with recombinant cauliflower mosaic virus or tobacco mosaic virus. In an exemplary insect cell system, *Autographa californica* nuclear polyhidrosis virus is used as a vector to express foreign genes in *Spodoptera frugiperda* cells or the Hi5 cell line (Invitrogen, Carlsbad, Calif.). Nucleic acid coding sequences are cloned into, for example, the polyhedrin gene of the virus under control of the polyhedrin promoter. Recombinant viruses containing the cloned gene are then used to infect *Spodoptera frugiperda* cells and the inserted gene is expressed (e.g., U.S. Pat. No. 4,215,051; Kitts et al., Biotechniques 14:810-817, 1993; Lucklow et al., J. Virol., 67:4566-79, 1993). Other exemplary insect cell expression vectors are based on baculovirus vectors, for example, pBlueBac (Invitrogen, Sorrento, Calif.).

An exemplary expression system in mammalian cell lines may utilize adenovirus as an expression vector. Coding sequences may be ligated to, e.g., the adenovirus late promoter. The cloned gene may be inserted into the adenovirus genome by in vitro or in vivo recombination. Insertion in a non-essential region of the viral genome (e.g., region E1 or E3) results in a recombinant virus that is capable of infecting and expressing cloned proteins in mammalian host cells. The disclosed examples are not limiting and any known expression vector may be used.

Cells transformed with expression vectors may be selected from non-transformed cells. A number of selection systems may be used, including but not limited to, the thymidine kinase gene, hypoxanthine-guanine phosphoribosyltransferase gene, methotrexate resistance gene, neomycin phosphotransferase gene and hygromycin resistance gene. These genes, contained in standard cloning vectors, either confer resistance to cytotoxic agents or allow cell growth in nutrient deficient medium.

Expressed proteins may be partially or completely purified before analysis. Protein purification may be facilitated by expressing cloned sequences as fusion proteins containing short leader sequences that allow rapid affinity purification. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). A leader sequence may be linked to a protein by a specific recognition site for a protease, allowing removal of the leader sequence prior to protein analysis. Examples of suitable protease recognition sequences include those recognized by the Tobacco Etch Virus protease (Life Technologies, Gaithersburg, Md.) or Factor Xa (New England Biolabs, Beverley, Mass.). Alternatively, expressed proteins may be purified by standard techniques discussed above.

Although the methods disclosed above are directed towards analysis of proteins, they are also applicable to the analysis of other types of analytes. For example, cells could be incubated in a labeled monosaccharide and polysaccharides could be purified and identified and/or sequenced as described herein. The labeled subunit (e.g., monosaccharide) may be derivatized to prevent its metabolism and conversion to a different structure. Subunits and polymeric forms of such analytes are known in the art.

Protein Labeling

Proteins to be analyzed may comprise labeled amino acid residues. Amino acids may be labeled by any methods known in the art. A labeled amino acid residue may be incorporated into a protein during synthesis. Alternatively, labels may be attached to amino acid residues by covalent or non-covalent bonding after protein synthesis.

Labels of use in the disclosed methods may include, but are not limited to, any composition detectable by electrical, optical, spectrophotometric, photochemical, biochemical, immunochemical, and/or chemical techniques. Labels may include, but are not limited to, conducting, luminescent, fluorescent, chemiluminescent, bioluminescent and phosphorescent labels, nanoparticles, metal nanoparticles, gold nanoparticles, silver nanoparticles, chromogens, antibodies, antibody fragments, genetically engineered antibodies, enzymes, substrates, cofactors, inhibitors, binding proteins, magnetic particles and spin labels.

Non-limiting examples of photodetectable labels that may be used include dansyl chloride, rhodamine isothiocyanate, TRIT (tetramethyl rhodamine isothiol), NBD (7-nitrobenz-2-oxa-1,3-diazole), Texas Red, phthalic acid, terephthalic acid, isophthalic acid, cresyl fast violet, cresyl blue violet, brilliant cresyl blue, para-aminobenzoic acid, erythrosine, biotin, digoxigenin, fluorescein, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, aminoacridine, 6-carboxyrhodamine, 6-carboxytetramethyl amino phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allophycocyanin, phycocyanin C, phycocyanin R, thiamine, phycoerythrocyanin, phycoerythrin R, luciferin, or acridinium esters. These and other luminescent labels may be obtained from commercial sources such as Molecular Probes (Eugene, Oreg.) and attached to amino acids by methods known in the art. Alternatively, certain pre-labeled amino acids are commercially available (e.g., Molecular Probes, Eugene, Oreg.).

Amino acid residues may be labeled with electrically detectable labels, such as metal nanoparticles. Gold or silver nanoparticles of between 1 nm and 3 nm in size may be used, although nanoparticles of different dimensions and mass may also be used. Methods of preparing nanoparticles are known. (See e.g., U.S. Pat. Nos. 6,054,495; 6,127,120; 6,149,868; Lee and Meisel, *J. Phys. Chem.* 86:3391-3395, 1982.) Nanoparticles may also be obtained from commercial sources (e.g., Nanoprobes Inc., Yaphank, N.Y.; Polysciences, Inc., Warrington, Pa.). Modified nanoparticles are available commercially, such as Nanogold® nanoparticles from Nanoprobes, Inc. (Yaphank, N.Y.). Nanogold® nanoparticles may be obtained with either single or multiple maleimide, amine or other groups attached per nanoparticle. The Nanogold® nanoparticles also are available in either positively or negatively charged form. Such modified nanoparticles may be attached covalently to amino acid residues either before or after the amino acid residues are incorporated into proteins. Nanoparticles or other labels may be attached to amino acid residues via any known linker compound to reduce steric hindrance and facilitate protein polymerization.

Labeled amino acid residues may be incorporated into proteins made from a nucleic acid template. Alternatively, labels may be attached to a particular type of amino acid residue after synthesis of the protein. In some methods, the label may be attached by antibody-antigen interactions. A label such as fluorescein or biotin may be attached to one end of a protein molecule, such as the N-terminal or C-terminal end.

Proteins may be post-translationally labeled using side-chain specific and/or selective reagents. Such reagents and methods for post-translational modification are known in the art. Non-limiting exemplary reagents that may be used include acetic anhydride (lysine, cysteine, serine and tyrosine); trinitrobenzenesulfonate (lysine); carbodiimides (glutamate, aspartate); phenylglyoxal (arginine); 2,3-butanedione (arginine); pyridoxal phosphate (lysine); p-chloromercuribenzoate (cysteine); 5,5'-dithiobis(2-nitro-benzoic acid) (cysteine); diethylpyrocarbonate (lysine, histidine); N-bromosuccinimide (tryptophan) and tetranitromethane (cysteine, tyrosine). Such reagents may be modified to attach various types of labels, such as Raman labels. Alternatively, Raman labels and/or gold nanoparticles that contain reactive groups for attachment to various types of amino acid side chains may be obtained from commercial sources (Molecular Probes, Eugene, Oreg.; Nanoprobes, Inc., Yaphank, N.Y.).

Various cross-linking reagents known in the art, such as homo-bifunctional, hetero-bifunctional and/or photoactivatable cross-linking reagents may be used to attach labels to proteins. Non-limiting examples of such reagents include bisimidates; 1,5-difluoro-2,4-(dinitrobenzene); N-hydroxysuccinimide ester of suberic acid; disuccinimidyl tartarate; dimethyl-3,3'-dithio-bispropionimidate; N-succinimidyl-3-(2-pyridyldithio)propionate; 4-(bromoaminoethyl)-2-nitro-phenylazide; and 4-azidoglyoxal. Methods of use of cross-linking reagents are well known in the art.

Nanopores, Nanochannels and Nanotubes

Labeled proteins or other polymers may be passed through one or more nanopores, nanochannels or nanotubes for analysis. As used herein, the terms nanopores, nanotubes and nanochannels are used interchangeably. The skilled artisan will realize that where the specification refers to a nanopore, different alternatives may use a nanochannel or nanotube. The only requirement is that the nanopore, nanochannel or nanotube connect one fluid filled compartment to another and allow the passage and detection of labeled proteins.

Size Characteristics

Nanopores of use may be about 0.5, 1, 2, 3, 4, 5, 6, 7, 8, 9 or 10 nm in diameter. However, the diameter may range between 1-3, 1-5, 1-10, 1-20, 1-50, 1-100, 5-10, 5-20, 10-20, 20-50, 30-75, 50-75, 50-100, 75-100, 100-300, 300-400, 400-500 or 100-999 nm. Nanopore diameter may be selected to pass a single protein at a time, in a linear configuration. In certain alternatives, nanopore diameter may be selected to be too small to pass a protein in a globular or folded conformation. The dimensions of various folded and unfolded proteins are known in the art and may be estimated by known techniques, such as filtration or ultracentrifugation. Proteins to be analyzed may be unfolded and/or partially or fully denatured by known methods to facilitate their passage through a nanopore in a linear conformation. Such methods may include, but are not limited to, exposure to media of either alkaline or acidic pH, use of high or low salt concentrations, use of detergents such as sodium dodecyl sulphate, octylglucoside or Triton X-100, use of chaotrophic agents such as urea or guanidinium, treatment with disulfide reducing agents such as dithiothreitol or mercaptoethanol, exposure to organic solvents, etc. Alternatively, linear peptides may be generated by limited proteolytic digestion of proteins. Where the amino acid residues are to be labeled with bulky groups, the nanopores may be larger to allow passage of labeled proteins. In alternatives that utilize nanotubes or nanochannels in place of nanopores, the same size considerations apply to the diameter or width of the nanotubes or nanochannels.

Fabrication of Nanopores, Nanotubes and Nanochannels

Fabrication of nanopores, nanotubes and/or nanochannels, individually or in arrays, may utilize any technique known in the art for nanoscale manufacturing. Nanopores, nanochannels and/or nanotubes may be constructed on a solid-state matrix comprising sensor layers using known nanolithography methods, including but not limited to chemical vapor deposition, electrochemical deposition, chemical deposition, electroplating, thermal diffusion and evaporation, physical vapor deposition, sol-gel deposition, focused electron beam, focused ion beam, molecular beam epitaxy, dip-pen nanolithography, reactive-ion beam etching, chemically assisted ion beam etching, microwave assisted plasma etching, electro-oxidation, scanning probe methods, chemical etching, laser ablation, or any other method known in the art (E.g., U.S. Pat. No. 6,146,227).

Nanopores, nanotubes and/or nanochannels may penetrate one or more sensor layers. The sensor layers may comprise semiconductor materials including, but not limited to, silicon, silicon dioxide, silicon nitride, germanium, gallinium arsenide, and/or metal-based compositions such as metals or metal oxides. Sensor layers may be processed by electronic beam, ion beam and/or laser lithography and etching to create a channel, groove, or hole. Conducting layers comprising metals may be deposited onto a semiconductor surface by means of field evaporation from a scanning tunnel microscope (STM) or atomic force microscope (AFM) tip or from a solution. Insulating layers may be formed by oxidizing the semiconductor's surface to an insulating composition.

Channels or grooves may be etched into a semiconductor surface by various techniques known in the art including, but not limited to, methodologies using an STM/AFM tip in an oxide etching solution. After channels are formed, two semiconductor surfaces may be opposed to create one or more nanopores or nanochannels that penetrate the semiconductor. STM tip methodologies may be used to create nanopores, nanodetectors, nanowires, nanoleads, nanochannels, and other nanostructures using techniques known in the art. Scanning probes, chemical etching techniques, and/or micromachining may be used to cut micrometer-dimensioned or nanometer-dimensioned channels, grooves or holes in a semiconductor substrate.

Nano-molding may be employed, wherein formed nanotubes, such as carbon or metallic nanotubes, are placed or grown on a semiconductor chip substrate. After depositing additional material on the substrate, the nanotubes are removed, leaving a nanochannel and/or nanopore imprint in the substrate material. Such nanostructures can be built in clusters with properties of molecular electrodes that may function as detectors.

Nanopores and/or nanochannels may be made using a high-throughput electron-beam lithography system. Electron-beam lithography may be used to write features as small as 5 nm on silicon chips. Sensitive resists, such as polymethyl-methacrylate, coated on silicon surfaces may be patterned without use of a mask. The electron-beam array may combine a field emitter cluster with a microchannel amplifier to increase the stability of the electron beam, allowing operation at low currents. The SoftMask™ control system may be used to control electron-beam lithography of nanoscale features on a semiconductor chip substrate.

Nanopores and/or nanochannels may be produced using focused atom lasers (e.g., Bloch et al., "Optics with an atom laser beam," *Phys. Rev. Lett.* 87:123-321, 1). Focused atom lasers may be used for lithography, much like standard lasers or focused electron beams. Such techniques are capable of producing micron scale or even nanoscale structures on a chip. In other alternatives, dip-pen nanolithography may be used to form nanochannels (e.g., Ivanisevic et al., "Dip-Pen Nanolithography on Semiconductor Surfaces," *J. Am. Chem. Soc.,* 123: 7887-7889, 1). Dip-pen nanolithograpy uses AFM techniques to deposit molecules on surfaces, such as silicon chips. Features as small as 15 nm in size may be formed, with spatial resolution of 10 nm. Nanoscale pores and/or channels may be formed by using dip-pen nanolithography in combination with regular photolithography techniques. For example, a micron scale line in a layer of resist may be formed by standard photolithography. Using dip-pen nanolithography, the width of the line and the corresponding diameter of the channel after etching may be narrowed by depositing additional resist compound. After etching of the thinner line, a nanoscale channel may be formed. Alternatively, AFM methods may be used to remove photoresist material to form nanometer scale features.

Ion-beam lithography may be used to create nanopores and/or nanochannels on a chip (e.g., Siegel, "Ion Beam Lithography," VLSI Electronics, Microstructure Science, Vol. 16, Einspruch and Watts Eds., Academic Press, New York, 1987). A finely focused ion beam may be used to write nanoscale features directly on a layer of resist without use of a mask. Alternatively, broad ion beams may be used in combination with masks to form features as small as 100 nm in scale. Chemical etching, for example, with hydrofluoric acid, may be used to remove exposed silicon or other chip material that is not protected by resist. The skilled artisan will realize that the techniques disclosed above are not limiting, and that nanopores and/or nanochannels may be formed by any method known in the art.

The surfaces of nanopores, nanotubes or nanochannels may be modified by coating, for example to transform a surface from a hydrophobic to a hydrophilic surface and/or to decrease adsorption of polymers such as proteins to a surface. Surface modification of common chip materials such as glass, silicon and/or quartz is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other known coating. Such coatings may not be appropriate where they would interfere with label detection, such as interfering with electrical conductivity using an electrical detector.

Carbon Nanotubes

Nanopores may comprise, be attached to or be replaced by nanotubes, such as carbon nanotubes. Carbon nanotubes may be coated with an organic or inorganic composition, leaving a deposited layer "mold" on the carbon nanotube. When the nanotube is removed and separated from the organic or inorganic deposit, a nanopore or nanochannel may be created in the "mold." Carbon nanotubes may be formed in a semiconductor with other components, such as sensor layers, formed around the nanotubes.

Carbon nanotubes may be manufactured by chemical vapor deposition (CVD), using ethylene and iron catalysts deposited on silicon (e.g., Cheung et al. PNAS 97:3809-3813, 2000). Single-wall carbon nanotubes may be formed on silicon chips by CVD using AFM $Si_3N_4$ tips (e.g., Cheung, et al., 2000; Wong, et al. Nature 394: 52-55, 1998). A flat surface of 1-5 $\mu m^2$ may be created on the silicon AFM tips by contact with silicon or CVD diamond surfaces (GE Suprabrasives, Worthington, Ohio) at high load (~1 $\mu N$), at high scan speed (30 Hz), and with a large scan size (40 $\mu m$) for several minutes. Approximately 100 nm diameter, 1 $\mu m$ deep pores in the ends of the AFM tips may be made by anodization at 2.1 V for 100 sec. Anodized tips may be etched in 0.03% KOH in water for 50 sec, after which excess silicon may be removed with ethanol, resulting in nanopores formed at the surface of the tip.

Carbon nanotubes may be attached to AFM tips using known methods. For example, iron catalyst consisting of iron oxide nanoparticles may be synthesized according to Murphy et al. (Austr. J. Soil Res. 13:189-201, 1975). Iron catalyst (0.5 to 4 nm particles) may be electrochemically deposited from a colloidal suspension into the pores using platinum counter electrodes at -0.5 V (Cheung, et al., 2000). Tips may be washed in water to remove excess iron oxide particles. AFM tips may be oxidized by heating in oxygen gas and carbon nanotubes may be grown on the catalyst by controlled heating and cooling in the presence of a carbon source (Murphy et al., 1975; Cheung et al., 2000). The diameter of the resulting nanotubes should correspond to the size of the iron oxide catalyst used (0.5 to 4 nm). Individual, single-walled nanotubes prepared under these conditions are aligned perpendicular to the flattened surface of the AFM tip. Residual iron catalyst may be removed by known methods.

Nanotubes may be cut to a predetermined length using known techniques. In some embodiments of the invention, carbon nanotubes may be attached to pyramids of gold-coated silicon cantilevers using an acrylic adhesive. The carbon nanotubes may be shortened to a defined length by application of a bias voltage between the tip and a niobium surface in an oxygen atmosphere (Wong, et al., Nature 394:52-55, 1998). Alternatively, high-energy beams may be used to shorten carbon nanotubes. Such high energy beams may include, but are not limited to, laser beams, ion beams, and electron beams. Alternative methods for truncating carbon nanotubes are known in the art (e.g., U.S. Pat. No. 6,283,812). Preformed carbon nanotubes may be attached to a chip material such as silicon, glass, ceramic, germanium, polystyrene, and/or gallium arsenide (e.g., U.S. Pat. Nos. 6,038,060 and 6,062,931).

A first set of carbon nanotubes may be used as cold cathode emitters on semiconductor chips, associated with a second set of nanotubes containing proteins. The first set of nanotubes may be used to create local electrical fields of at least $10^6$ volts/cm, when an external voltage of between 10 and 50 volts is applied. Such an electric field in the first set of nanotubes can be used to drive proteins through the second set of nanotubes, or to generate an electrical or electromagnetic signal to detect labeled amino acid residues (Chuang, et al., 2000; U.S. Pat. No. 6,062,931). Electromagnetic radiation from a third set of nanotubes may excite a luminescent label attached to a protein passing through a second set of nanotubes, leading to emission of light detected by a photodetector that is operably coupled to a first set of nanotubes.

Ion Channels on Semiconductor Chips

Nanopores may comprise single ion channels in lipid bilayer membranes (e.g., Kasianowitz, et al., Proc. Natl. Acad. Sci. USA 93:13770-13773, 1996). Such ion channels may include, but are not limited to, *Staphylococcus aureus* alpha-hemolysin and/or mitochondrial voltage-dependent anion channels. These ion channels may remain open for extended periods of time. An electric field applied to proteins can cause these molecules to move through ion channels in lipid bilayer membranes. Ion channels may be incorporated into chips and operably coupled to detectors.

Micro-Electro-Mechanical Systems (MEMS)

Nanopores, sensor layers and other components of the disclosed apparatus may be incorporated into one or more Micro-Electro-Mechanical Systems (MEMS). MEMS are integrated systems that may comprise mechanical elements, actuator elements, control elements, detector elements and/or electronic elements. All of the components may be manufactured by known microfabrication techniques on a common chip, comprising a silicon-based or equivalent substrate (e.g., Voldman et al., Ann. Rev. Biomed. Eng. 1:401-425, 1999).

The electronic components of MEMS may be fabricated using integrated circuit (IC) processes (e.g., CMOS, Bipolar, or BICMOS processes). They may be patterned using photolithographic and etching methods known for semiconductor chip manufacture. The micromechanical components may be fabricated using "micromachining" processes that selectively etch away parts of the silicon wafer and/or add new structural layers to form the mechanical and/or electromechanical components. Basic techniques in MEMS manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. Sensor layers, of 5 nm thickness or less may be formed by such known techniques. Standard lithography techniques may be used to create sensor layers of micron or sub-micron dimensions, operably coupled to detectors and nanopores.

The manufacturing method is not limiting and any methods known in the art may be used, such as atomic layer deposition, pulsed DC magnetron sputtering, vacuum evaporation, laser ablation, injection molding, molecular beam epitaxy, dip-pen nanolithograpy, reactive-ion beam etching, chemically assisted ion beam etching, microwave assisted plasma etching, focused ion beam milling, electron beam or focused ion beam technology or imprinting techniques. Methods for manufacture of nanoelectromechanical systems may be used. (See, e.g., Craighead, Science 290:1532-36, 0.)

It is contemplated that some or all of the components of the apparatus may be constructed as part of an integrated MEMS device. Nanoelectrodes comprising conducting metals such as gold, platinum, or copper may be operably coupled to nanopores, nanochannels and/or nanotubes using STM technologies known in the art (e.g., Kolb et al., Science 275:1097-1099, 1997). Nanoelectrodes, detectors and other components may be connected by nanowires.

Detectors

Photodetectors

Amino acid residues labeled with photolabels may be detected using an excitatory light source and a photodetector (e.g., Sepaniak et al., J. Microcol. Separations 1:155-157, 1981; Foret et al., Electrophoresis 7:430-432, 1986; Horokawa et al., J. Chromatog. 463:39-49 1989; U.S. Pat. No. 5,302,272). Exemplary light sources include diode-lasers, vertical cavity surface-emitting lasers, edge-emitting lasers, surface emitting lasers and quantum cavity lasers, for example a Continuum Corporation Nd-YAG pumped Ti:Sapphire tunable solid-state laser and a Lambda Physik excimer pumped dye laser. Exemplary photodetectors include photodiodes, avalanche photodiodes, photomultiplier tubes, multi-anode photomultiplier tubes, phototransistors, vacuum photodiodes, silicon photodiodes, fiber-optic or phototransistor detectors and charge-coupled devices (CCDs). An avalanche photodiode (APD) may be used to detect low light levels. The APD process uses photodiode arrays for electron multiplication effects (U.S. Pat. No. 6,197,503).

A photodetector, light source and nanopore may be fabricated into a semiconductor chip using known N-well Complementary Metal Oxide Semiconductor (CMOS) processes (Orbit Semiconductor, Sunnyvale, Calif.). Alternatively, the detector, light source and nanopore may be fabricated in a silicon-on-insulator CMOS process (e.g., U.S. Pat. No. 6,117,643). In other alternatives, an array of diode-laser illuminators and CCD detectors may be placed on a semiconductor chip (U.S. Pat. Nos. 4,874,492 and 5,061,067; Eggers et al., BioTechniques 17: 516-524, 1994).

A photodetector may be positioned perpendicular to a light source to minimize background light. The light source may be optically separated from the photodetector by one or more light opaque layers. Photons generated by excitation of luminescent labels may be collected by a fiber optic and transferred to a CCD detector on a chip (e.g., U.S. Pat. No. 6,274, 320). The times at which labeled amino acid residues are detected may be recorded and amino acid residue distance maps may be constructed.

Light sources, such as light-emitting diodes and/or semiconductor lasers may be incorporated into semiconductor chips (U.S. Pat. No. 6,197,503). Diffractive optical elements that shape a laser or diode light beam may also be integrated into a chip. An air-cooled argon laser at 488 nm may be used to excite fluorescein-labeled proteins. Emitted light may be collected by an optics system comprising a fiber optic, a lens, an imaging spectrometer, and a 0° C. thermoelectrically-cooled CCD camera. Alternative examples of photodetectors are known in the art (e.g., U.S. Pat. No. 5,143,8545).

Raman Spectroscopy

Labeled amino acid residues may be detected by Raman spectroscopy. Raman labels of use in spectrophotometric detection are well known in the art (e.g., U.S. Pat. Nos. 5,306,403; 6,002,471; 6,174,677). Labeled amino acid residues may be excited with a laser, photodiode, or other light source and the excited amino acid residue detected by a variety of Raman techniques, including but not limited to surface enhanced Raman spectroscopy (SERS), surface enhanced resonance Raman spectroscopy (SERRS) normal Raman scattering, resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy. In SERS and SERRS, the sensitivity of the Raman detection is enhanced by a factor of $10^6$ or more for molecules adsorbed on roughened metal surfaces, such as silver, gold, platinum, copper or aluminum surfaces. Portions of the nanopores and/or sensor layers may be coated with a Raman sensitive metal, such as silver or gold to provide an enhanced Raman signal.

FRET Detection

A protein may also be analyzed using fluorescence resonance energy transfer (FRET). FRET is a spectroscopic phenomenon used to detect proximity between fluorescent donor and acceptor molecules. The donor and acceptor pairs are chosen such that fluorescent emission from the donor overlaps the excitation spectrum of the acceptor. When the two molecules are associated at a distance of less than 100 Angstroms, the excited-state energy of the donor is transferred non-radiatively to the acceptor. If the acceptor molecule is a fluorophore then its emission is enhanced. Compositions and methods for use of FRET are known (e.g., U.S. Pat. No. 5,866,336).

The donor fluorophore molecules may be attached to an amino acid residue, and the acceptor fluorophore molecules may be connected to a nanopore or sensor layer. Following excitation by a light source, the donor fluorophore molecules may transfer their energy to the acceptor molecules, resulting in an enhanced fluorescent signal from the acceptor molecules that may be detected by a photodetector.

Electrical Detectors

An electrical detector may detect electrical signals from a conducting layer as a labeled protein passes through a nanopore. Non-limiting examples of electrical signals include current, voltage, impedance, capacitance, electromotive force, signal sign, frequency or noise signature measured across a nanopore. An electrical detector may be operably coupled to one or more conducting layers, a power supply and one or more nanopores penetrating the conducting layers. The detector may comprise an ammeter, voltmeter, capacitance meter and/or conductivity meter, etc. Other electrical components such as resistors and/or capacitors may be included in the electrical circuit associated with the detector.

In certain methods, first and second buffer chambers may be filled with a low conductivity aqueous buffer. An electrical potential may be applied to conducting layers flanking a nanopore. When buffer alone is present, the resistance between the conducting layers is high. The presence of unlabeled regions of proteins passing through the nanopore may produce a slight increase in conductivity across the nanopore. The passage of amino acid residues labeled with highly conductive labels, such as metal nanoparticles, would result in an increase in conductivity that produces a detectable signal at the detector. The time interval between detectable electrical signals may be measured and used to create a distance map representing the positions of labeled amino acid residues on the protein molecule for each type of labeled amino acid. The distance map(s) may be used to identify the protein by comparison with known protein sequences. By compiling such maps for each of the twenty types of amino acid residues it would be possible to determine a complete sequence of the protein.

EXAMPLES

Example 1

Apparatus for Protein Identification and/or Sequencing

Figure 2:
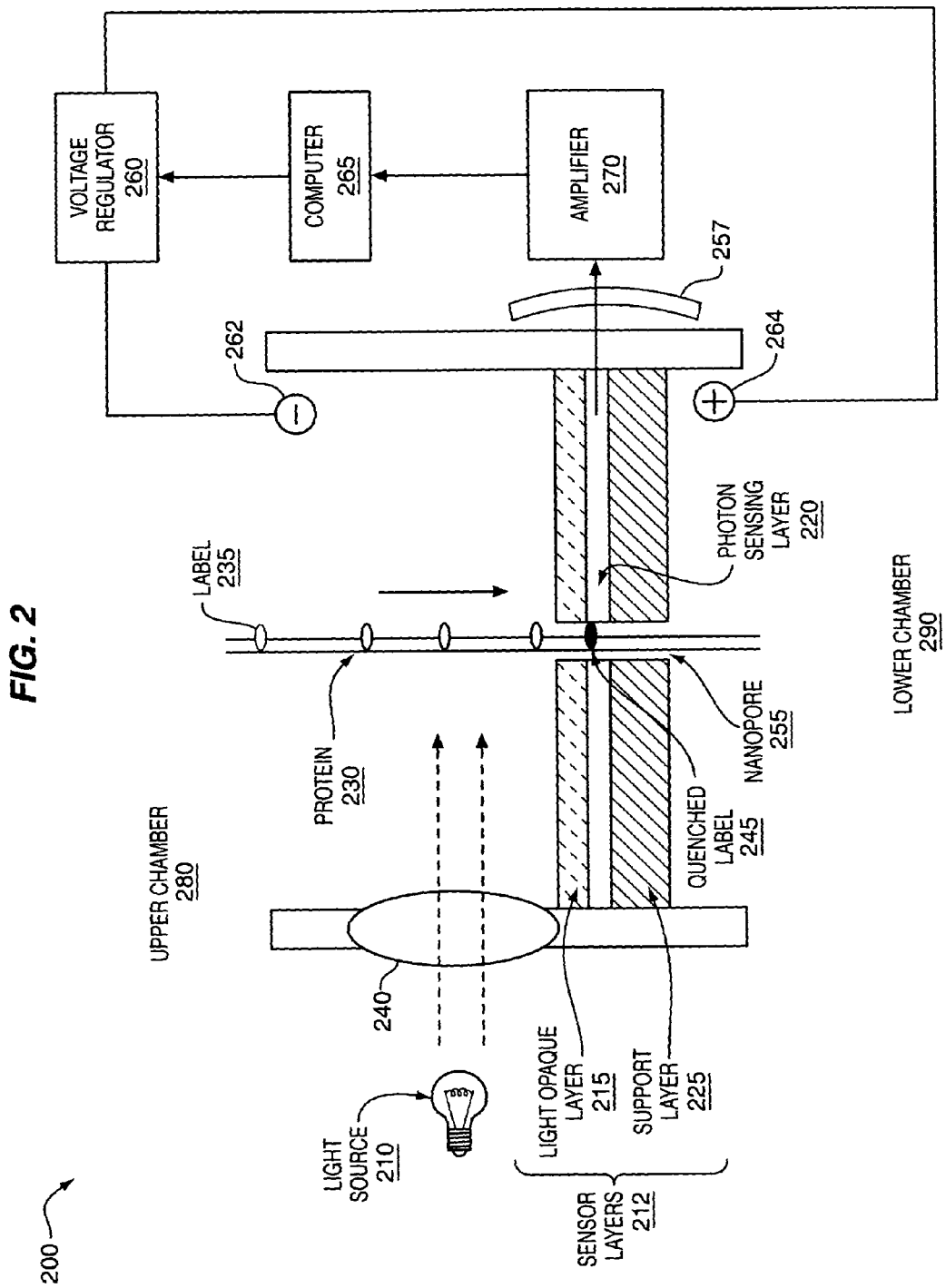
FIG. 2 illustrates a non-limiting example of a sub-device 200 (not to scale) for protein 230 sequencing and/or identification by photodetection.
Figure 3:
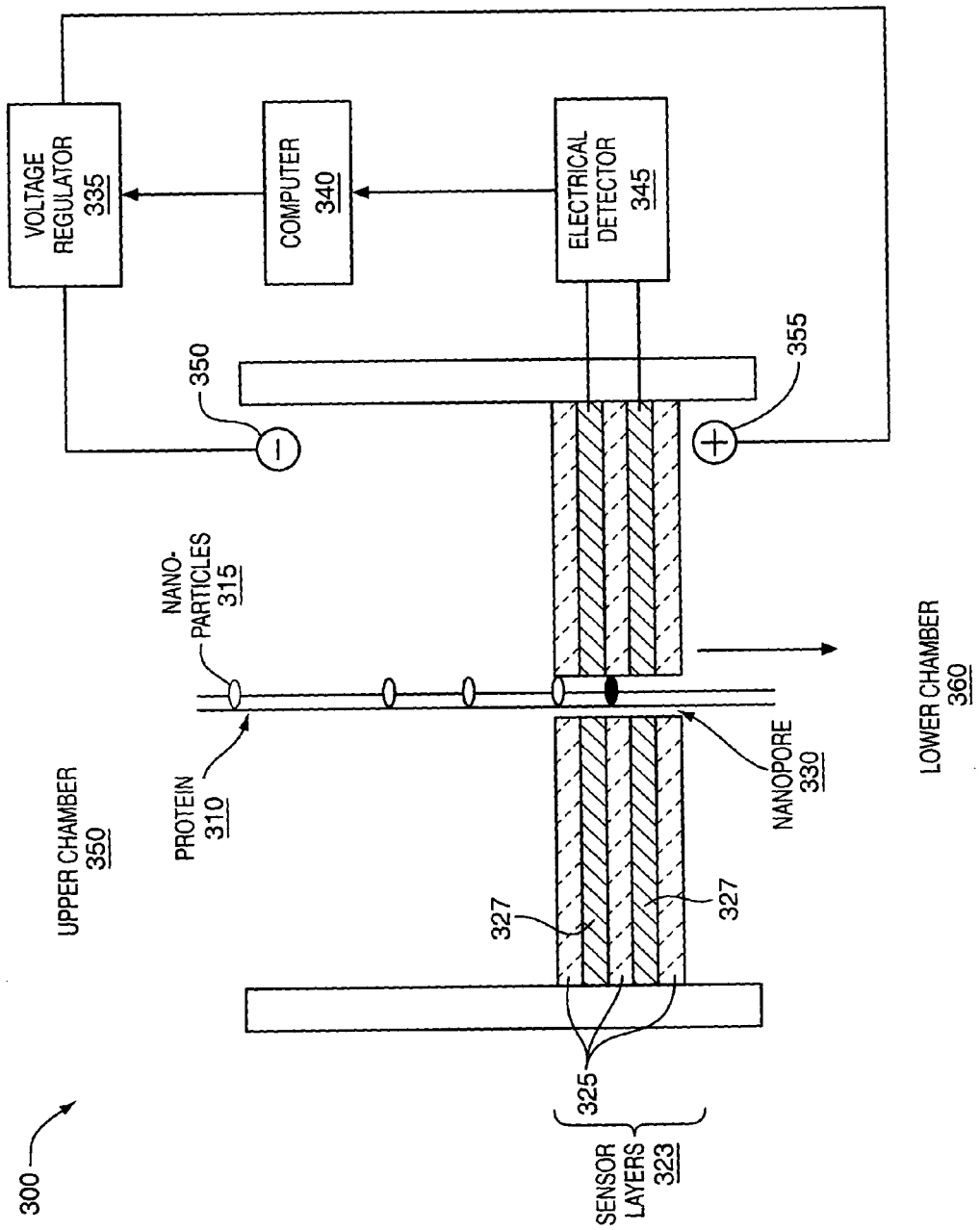
FIG. 3 illustrates another non-limiting example of a sub-device 300 (not to scale) for protein 310 sequencing and/or identification by electrical detection.

FIG. 2 and FIG. 3 provide non-limiting examples of methods and apparatus for protein 230, 310 analysis. An apparatus may comprise one or more sub-devices 200, 300. Each sub-device 200, 300 may comprise fluid filled first 280, 350 and second 290, 360 chambers, separated by sensor layers 212, 323. One or more nanopores 255, 330 may extend through the sensor layers 212, 323 and allow passage of labeled proteins 230, 310. The nanopores 255, 330 may be operably coupled to one or more detectors 257, 345 that can detect labeled amino acid residues 235, 245, 315 as they pass through the nanopores 255, 330. Electrodes 262, 264, 350, 355 in the first and second chambers 280, 350, 290, 360 may be used to generate an electrical field that drives labeled proteins 230, 310 from the first 280, 350 to the second chamber 290, 360 through the nanopores 255, 330. The electrical gradient may be controlled by a voltage regulator 260, 335, which may be operably coupled to a computer 265, 340. The nature of the electrical gradient is not limiting and the applied voltage may be alternating current, direct current, pulse field direct current, reverse phase current or any other known type of electrical gradient.

Sensor Layer Construction

As illustrated in FIG. 3, photolithography may be used to create an array of multiplaner structures (0.5×0.5 μm) on a silicon substrate, each structure with a silicon base support and one or more layers of gold film or other conductive layers 327 separated by one or more insulator layers 325 comprising, for example, silicon oxide. Other insulator layers 325 overlay the top and bottom conducting layers 327 and insulate the sensor layers 323 from the medium in the first 350 and second 360 chambers. Conducting and insulating layers 325, 327 may be formed on a chip by standard semiconductor technologies.

A chip containing the multiplanar structures may be divided into two or more parts. A layer of resist may be coated on the sides of each chip part, perpendicular to the conducting and insulating layers. An AFM/STP tip may be used to etch 5-10 nm lines in the resist layer overlaying each structure. Chemical etching may be used to create nano-scale grooves in each of the structures. When the chip parts are aligned and fused together, the grooves form nanopores 330 that extend through the sensor layers 323. Nanowires connecting the conducting layers 327 to electrical detectors 345 may be formed by known methods discussed above. The nanowires may be used to apply a voltage across the conducting layers 327. Changes in current, resistance and/or other electrical properties may be detected with the passage of a protein 310 labeled with electrically conductive labels, like gold nanoparticles 315, through the nanopore 330. A thin layer of insulating material may be formed on the sides of the divided chip prior to lithography and etching to prevent current flow except through the nanopore 330.

In alternative devices 200, exemplified in FIG. 2, the sensor layers 212 may comprise one or more light opaque layers 215 and photon sensing layers 220, overlaying a support layer 225, for photodetection of amino acid residues tagged with photolabels 235, 245. The light opaque layers 215 may be formed of any known light opaque material, for example a thin layer of chrome, silver or gold metal. Similarly, photon sensing layers 220 may be comprised of any material that is relatively translucent at the wavelengths of light emitted by the photolabel 235, 245 for example glass, silicon or certain types of plastics.

A wide variety of materials and structures are of use for photon sensing layers 220. In certain non-limiting examples, the photon sensing layer 220 may serve to simply conduct light to the photon sensing elements of a photodetector 257. In other alternatives, the photon sensing element may be integrated into the nanopore 255. For example, a photon sensitive PN junction may be directly fabricated into the photon sensing layer 220 surrounding a nanopore 255 by layering with different types of materials (e.g., P-doped and N-doped silicon or gallium arsenide (GaAs)) or by coating the inner surface of the nanopore 255 with a different type of semiconductor material. Methods for forming layers of P-doped and N-doped semiconductors are well known in the arts of computer chip and/or optical transducer manufacture. A photon transducer transduces a photonic signal into an electrical signal counterpart. Different types of known photon transducing structures that may be used to detect light emission include those based on photoconductive materials, photovoltaic cells (photocells), photoemissive materials (photomultiplier tubes, phototubes) and semiconductor pn junctions (photodiodes).

In a photoconductive cell, a semiconductor such as CdS, PbS, PbSe, InSb, InAs, HgCdTe or PbSnTe, behaves like a resistor. The semiconductor is in series with a constant voltage source and a load resistor. The voltage across the load resistor is used to measure the resistance of the semiconductor material. Incident radiation, for example in the form of an emitted photon from a tagged amino acid residue, causes band-gap excitation and lowers the resistance of the semiconductor.

A photodiode contains a reverse-bias semiconductor pn junction. The p-type semiconductor (e.g., boron doped silicon, beryllium doped GaAs) has excess electron holes, while the n-type semiconductor (e.g., phosphorus doped silicon, silicon doped GaAs) has excess electrons. Under a reverse bias, a depletion layer forms at the pn junction between the p-type and n-type semiconductors. A reverse bias is initiated when an external electrical potential is applied that forces electron holes in the p-type semiconductor and excess electrons in the n-type semiconductor to migrate away from the pn junction. When the material is irradiated, electron-hole pairs are formed that move under bias, resulting in a temporary electrical current across the pn junction. Photodiodes and other types of photon transducing structures may be incorporated into a nanopore 255 and used as photon sensing elements of a photodetector 257.

Polymeric materials may be coated on the chip to enhance signal detection. Such polymeric materials may include, but are not limited to, polymethylmethacrylate, ultraviolet-curable polyurethanes and epoxies, and other polymers that exhibit optical transparency, low fluorescence at excitation wavelengths, electrical conductivity and/or insulation. Such materials may be formed into appropriate structures, for example by polymer casting and chemical or photochemical curing (Kim et al., Nature 376: 581-584 1995).

Example 2

Photodetection

As illustrated in FIG. 2, amino acid residues labeled with a photolabel 235 may be excited by a light source 210, such as a laser. Excitatory light may pass through a transparent window 240 in the first chamber 280, exciting the photolabel 235 to a higher energy state. The labeled amino acid passes through the light opaque layer 215, cutting off the source of excitatory light and shielding the photodetector 257 from the light source 210. As the photolabel 235 passes the photon sensing layer 220, it emits a photon and returns to an unexcited state 245. The emitted photon may be detected by a photodetector 257. The detected signal may be amplified by an amplifier 270 and stored and/or processed by a computer 265. The computer 265 may also record the time at which each labeled amino acid passes through the nanopore 255, allowing the calculation of distances between adjacent labeled amino acid residues and the compilation of a distance map for each type of labeled amino acid.

In exemplary methods, a highly sensitive cooled CCD detector 257 may be used. The cooled CCD detector 257 has a probability of single-photon detection of up to 80%, a high spatial resolution pixel size (5 microns), and sensitivity in the visible through near infrared spectra. (Sheppard, Confocal Microscopy: Basic Principles and System Performance in: Multidimensional Microscopy, Cheng et al. Eds., Springer-Verlag, New York, N.Y. pp. 1-51, 1994.) In other examples, a coiled image-intensified coupling device (ICCD) may be used as a photodetector 257 that approaches single-photon counting levels (U.S. Pat. No. 6,147,198). A nanochannel plate operates as photomultiplier tube wherein a small number of photons triggers an avalanche of electrons that impinge on a phosphor screen, producing an illuminated image. This phosphor image is sensed by a CCD chip region 257 attached to an amplifier 270 through a fiber optic coupler. A CCD detector 257 on the chip may be sensitive to ultraviolet, visible, and/or infrared spectra light (U.S. Pat. No. 5,846,708).

Example 3

Electrical Detection

As illustrated in FIG. 3, amino acid residues may be tagged with a label 315 that can be detected by its electrical properties. In one non-limiting example, the label 315 may comprise gold nanoparticles 315. As an amino acid residue attached to a gold nanoparticle 315 passes through a nanopore 330, it produces detectable changes in the conductivity, resistance and other electrical properties of the nanopore 330. The conducting layers 327 flanking a nanopore 330 may be operably coupled to an electrical detector 345, which may detect any type of electrical signal, such as voltage, conductance, resistance, capacitance, etc. The detector 345 may be operably coupled to a computer 340 to process and store data. Distance maps showing distances between labeled amino acid residues may be constructed and used to identify and/or sequence the labeled protein.

A nanopore 2 to 5 nm in diameter may provide fluid communication between the first 350 and second 360 chambers. Proteins 310 labeled with 1 nm gold nanoparticles 315 may be synthesized and/or placed in the first chamber 350. An electrical detector 345, such as a voltage detector 345, and power supply may be operably coupled to conducting layers 327 flanking the nanopore 330. Current across the nanopore 330 may be converted to voltage and amplified using an AxopatchA (Axon Instruments, Foster City, Calif.) or a Dagan 3900A patch clamp amplifier (Dagan Instruments, Minneapolis, Minn.). The signal may be filtered using a Frequency Devices (Haverhill, Mass.) low pass Bessel filter. Data may be digitized using a National Instruments (Austin, Tex.) AT-MIO-16-X 16-bit board and LAB WINDOWS/CVI programs. The chip may be shielded from electric and magnetic noise sources using a mu-metal box (Amuneal, Philadelphia, Pa.) (see Kasianowicz, et al., 1996).

Example 4

Labeling of Proteins

Figure 4:
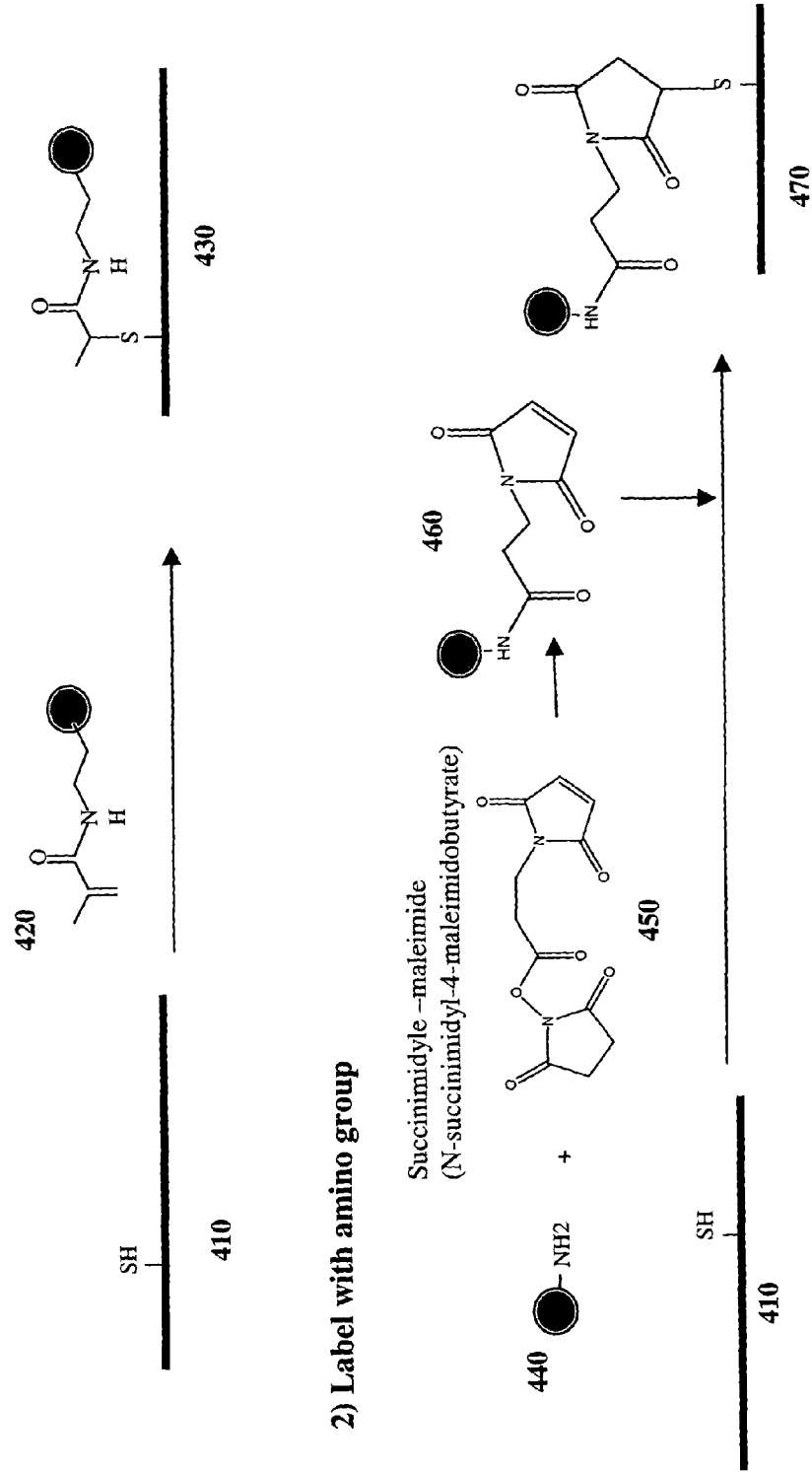
FIG. 4 shows non-limiting examples of protein labeling on cysteine residues.

Exemplary methods for protein labeling are disclosed in FIG. 4 through FIG. 7. As shown in FIG. 4, cysteine residues may be specifically tagged using sulfhydryl specific reagents. Naturally occurring cysteine residues in proteins 410 may be reduced from disulfides through exposure to known thiol reducing agents, such as dithiothreitol or β-mercaptoethanol. After removal of excess reducing agent, for example by ultrafiltration or column chromatography on a gel permeation column, the protein 410 containing reduced cysteine residues may be tagged by using a thiol specific reagent 420. In one non-limiting example, an acrydite label 420 may be reacted with endogenous cysteines to generate a labeled protein 430. Alternatively, an amine label 430 may be activated by exposure to N-succinimidyl-4-maleimidobutyrate 450. The activating group 450 covalently binds to the amine label 440. The activated complex 460 then binds to sulfhydryl groups, resulting in formation of a labeled protein 470.

Figure 5:
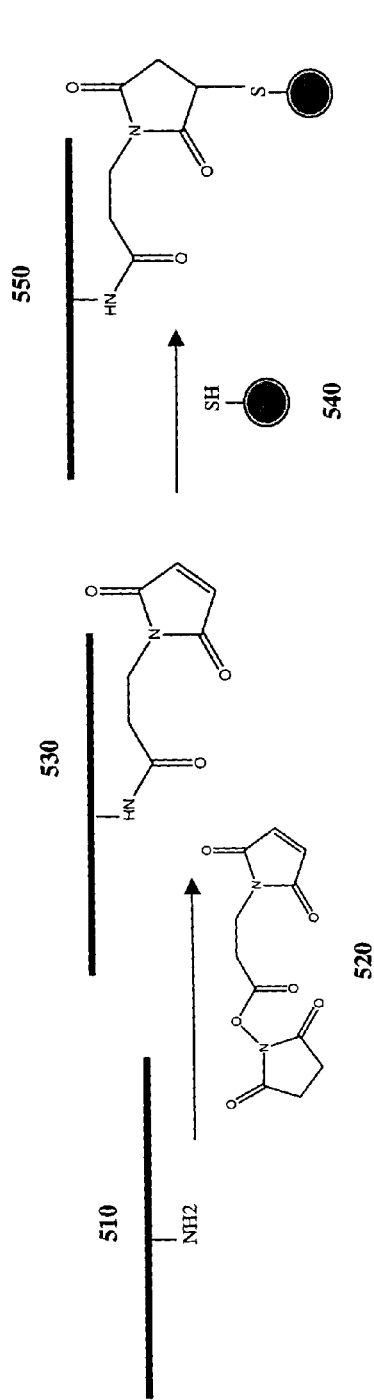
FIG. 5 shows non-limiting examples of protein labeling on lysine, arginine and N-terminal residues.
Figure 5:
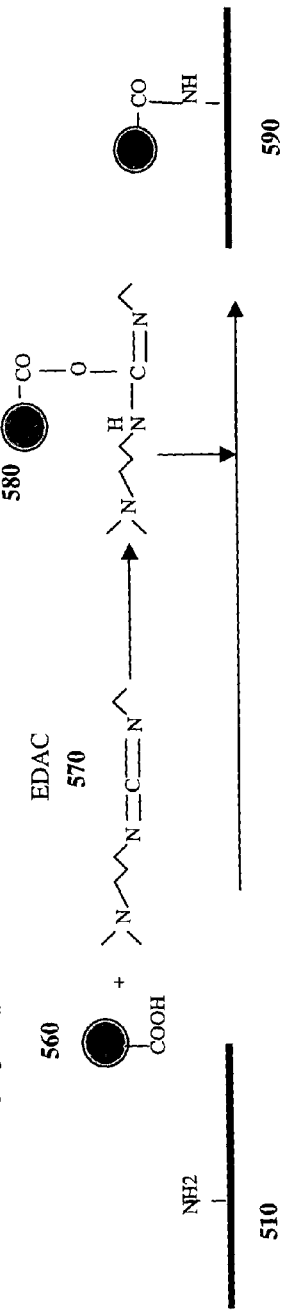

FIG. 5. illustrates exemplary methods of labeling proteins 510 on amine residues, such as lysine, arginine and the N-terminal residue of the protein 510. As shown in FIG. 5, amine residues on a protein 510 may be activated by reaction with a reagent 520, such as N-succinimidyl-4-maleimidobutyrate. The activated protein 530 may then be reacted with a thiolated label 540, resulting in covalent bond formation and production of a labeled protein 550. In another non-limiting example, a water soluble carbodiimide 570, such as EDAC (1-ethyl-3-(3-dimethlaminopropyl)carbodiimide) may be used to cross-link amine residues on a protein 510 with a carboxylated label 560. The carbodiimide 570 binds to and activates the label to form an activated intermediate 580, which can covalently bond with amine residues. The carbodiimide activating group 570 is eliminated and a labeled protein 590 is formed.

Figure 6:
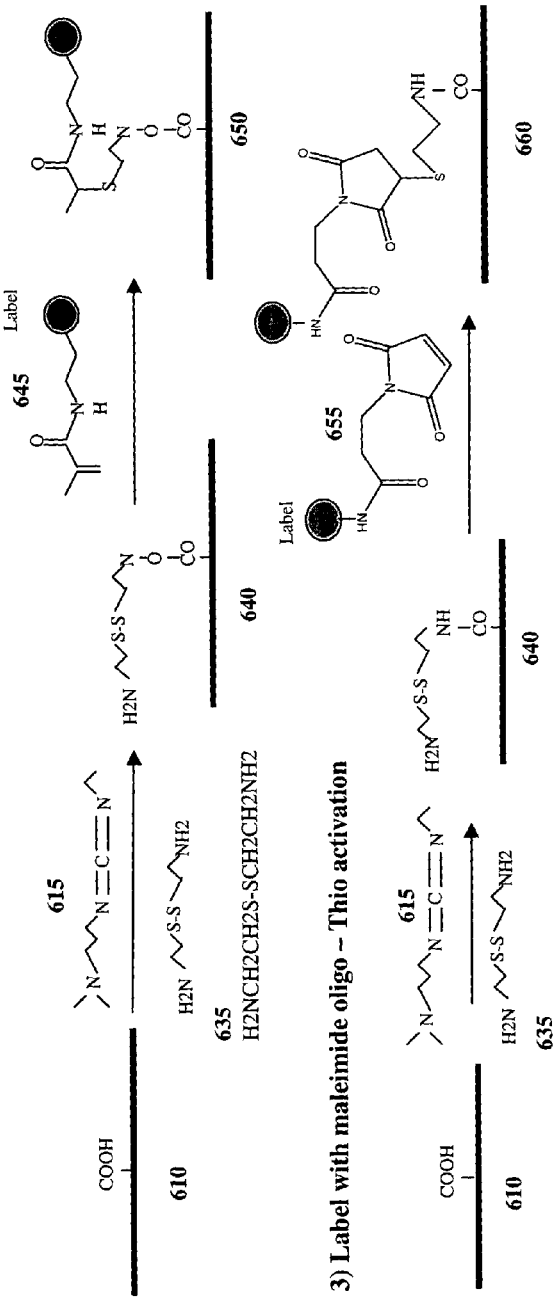
FIG. 6 shows non-limiting examples of protein labeling on aspartate, glutamate and C-terminal residues.

FIG. 6 shows exemplary methods of protein 610 labeling on carboxyl residues, such as glutamate, aspartate and the C-terminal residue. A protein 610 containing carboxyl residues may be activated by reaction with a water-soluble carbodiimide 615, such as EDAC, and then reacted with an amine label 625 to form a labeled protein 630. Alternatively, carboxyl residues on a protein 610 may be activated by reaction with both EDAC 615 and cystamine 635. This results in formation of a disulfide modified protein 640, which can react with an acrydite label 645 to form a labeled protein 650. In another alternative, carboxyl residues on a protein 610 may be activated by reaction with EDAC 615 and cystamine 635 and the activated protein 640 reacted with a maleimide label 655, resulting in formation of a labeled protein 660.

Figure 7:
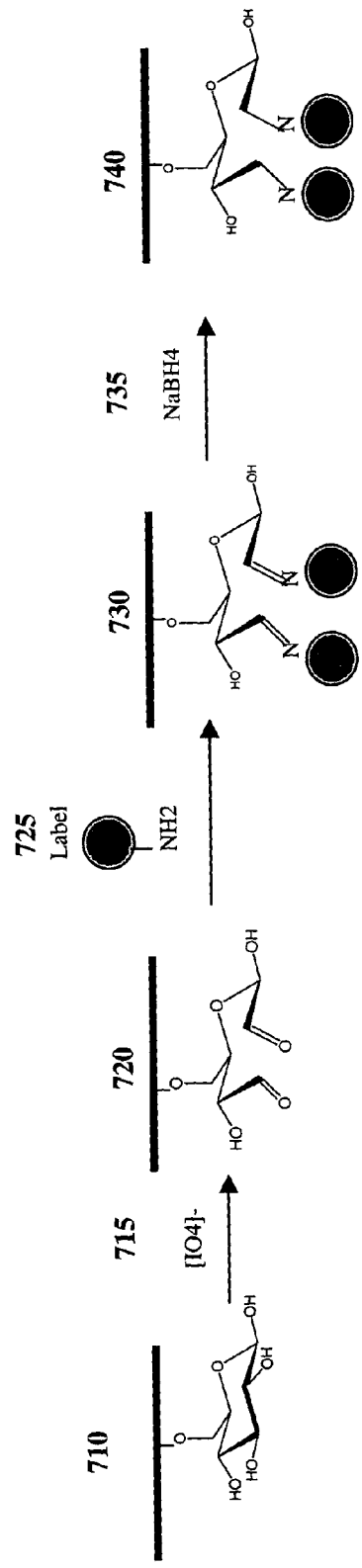
FIG. 7 shows non-limiting examples of protein labeling on serine and threonine residues.
Figure 7:
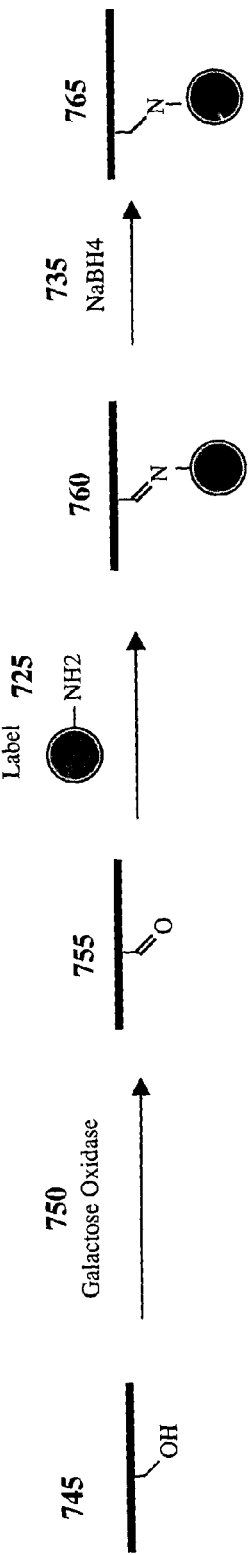

FIG. 7 illustrates exemplary methods of labeling proteins 710, 745 on serine, threonine residues or glycosylated residues. Glycoproteins 710 may be oxidized with periodate 715 to produce a dialdehyde sugar derivative 720. The dialdehyde 720 will react spontaneously with amine labels 725 to form a Shiff's base labeled protein 730. The Shiff's base 730 reaction is reversible. Reduction with sodium borohydride 735, for example, results in an irreversibly labeled protein 740. In another alternative, serine or threonine residues on a protein 745 may be oxidized, for example with galactose oxidase 750, to form an aldehyde derivatized protein 755. The aldehyde derivatized protein 755 may react with an amine label 725 to form a Shiff's base labeled protein 760. Again, reduction with sodium borohydride 735 produces an irreversibly labeled protein 765.

The skilled artisan will realize that the disclosed methods are exemplary only. Many methods for side-chain specific protein labeling are known in the art (e.g., Bell and Bell, Proteins and Enzymes, Ch. 7, pp. 132-183, Prentice-Hall, Inc., Englewood Cliffs, N.J., 1988) and any such known method may be used to label proteins with a photolabel, electrical label, or any other type of label disclosed herein or otherwise known in the art.

Example 5

Raman Detection of Analytes

Methods and Apparatus

In certain non-limiting methods, Raman spectroscopy may be used for analysis of analytes. In a non-limiting example, the excitaiton beam of a Raman detection unit was generated by a titanium:sapphire laser (Mira by Coherent) at a near-infrared wavelength (750~950 nm) or a gallium aluminum arsenide diode laser (PI-ECL series by Process Instruments) at 785 nm or 830 nm. Pulsed laser beams or continuous beams were used. The excitation beam was passed through a dichroic mirror (holographic notch filter by Kaiser Optical or a dichromatic interference filter by Chroma or Omega Optical) into a collinear geometry with the collected beam. The transmitted beam passed through a microscope objective (Nikon LU series), and was focused onto the Raman active substrate where target analytes (nucleotides or purine or pyrimidine bases) were located.

The Raman scattered light from the analytes was collected by the same microscope objective, and passed the dichroic mirror to the Raman detector. The Raman detector comprised a focusing lens, a spectrograph, and an array detector. The focusing lens focused the Raman scattered light through the entrance slit of the spectrograph. The spectrograph (Acton Research) comprised a grating that dispersed the light by its wavelength. The dispersed light was imaged onto an array detector (back-illuminated deep-depletion CCD camera by RoperScientific). The array detector was connected to a controller circuit, which was connected to a computer for data transfer and control of the detector function.

For surface-enhanced Raman spectroscopy (SERS), the Raman active substrate consisted of metallic nanoparticles or metal-coated nanostructures. Silver nanoparticles, ranging in size from 5 to 200 nm, was made by the method of Lee and Meisel (J. Phys. Chem., 86:3391, 1982). Alternatively, samples were placed on an aluminum substrate under the microscope objective. The Figures discussed below were collected in a stationary sample on the aluminum substrate. The number of molecules detected was determined by the optical collection volume of the illuminated sample. Detection sensitivity down to the single molecule level was demonstrated.

Single nucleotides may also be detected by SERS using a 100 μm or 200 μm microfluidic channel. Nucleotides may be delivered to a Raman active substrate through a microfluidic channel (between about 5 and 200 μm wide). Microfluidic channels may be made by molding polydimethylsiloxane (PDMS), using the technique disclosed in Anderson et al. ("Fabrication of topologically complex three-dimensional microfluidic systems in PDMS by rapid prototyping," Anal. Chem. 72:3158-3164, 2000).

Where SERS was performed in the presence of silver nanoparticles, the nucleotide, purine or pyrimidine analyte was mixed with LiCl (90 μM final concentration) and nanoparticles (0.25 M final concentration silver atoms). SERS data were collected using room temperature analyte solutions.

Oligonucleotides prepared by rolling circle amplification were also analyzed by Raman spectroscopy. One picomole (pmol) of a rolling circle amplification (RCA) primer was added to 0.1 pmol of circular, single-stranded M13 DNA template. The mixture was incubated with 1× T7 polymerase 160 buffer (20 mM (millimolar) Tris-HCl, pH 7.5, 10 mM $MgCl_2$, 1 mM dithiothreitol), 0.5 mM dNTPs and 2.5 units of T7 DNA polymerase for 2 hours at 37° C., resulting in formation of an RCA product. A negative control was prepared by mixing and incubating the same reagents without the DNA polymerase.

One µL of the RCA product and 1 µL of the negative control sample were separately spotted on an aluminum tray and air-dried. Each spot was rinsed with 5 µL of 1×PBS (phosphate buffered saline). The rinse was repeated three times and the aluminum tray was air-dried after the final rinse. One milliliter of silver colloid solution was diluted with 2 mL of distilled water. Eight microliters of the diluted silver colloid solution was mixed with 2 µL of 0.5 M LiCl and added to the RCA product spot on the aluminum tray. The same solution was added to the negative control spot. The Raman signals were collected as disclosed above.

Results

Nucleoside monophosphates, purine bases and pyrimidine bases were analyzed by SERS, using the system disclosed above. Table 1 shows the present detection limits for various analytes.

TABLE 1

SERS Detection of Nucleoside Monophosphates, Purines and Pyrimidines

| Analyte | Final Concentration | Number of Molecules Detected |
|---|---|---|
| dAMP | 9 picomolar (pM) | ~1 molecule |
| Adenine | 9 pM | ~1 molecule |
| dGMP | 90 µM | $6 \times 10^6$ |
| Guanine | 909 pM | 60 |
| dCMP | 909 µM | $6 \times 10^7$ |
| Cytosine | 90 nM | $6 \times 10^3$ |
| dTMP | 9 µM | $6 \times 10^5$ |
| Thymine | 90 nM | $6 \times 10^3$ |

Figure 8:
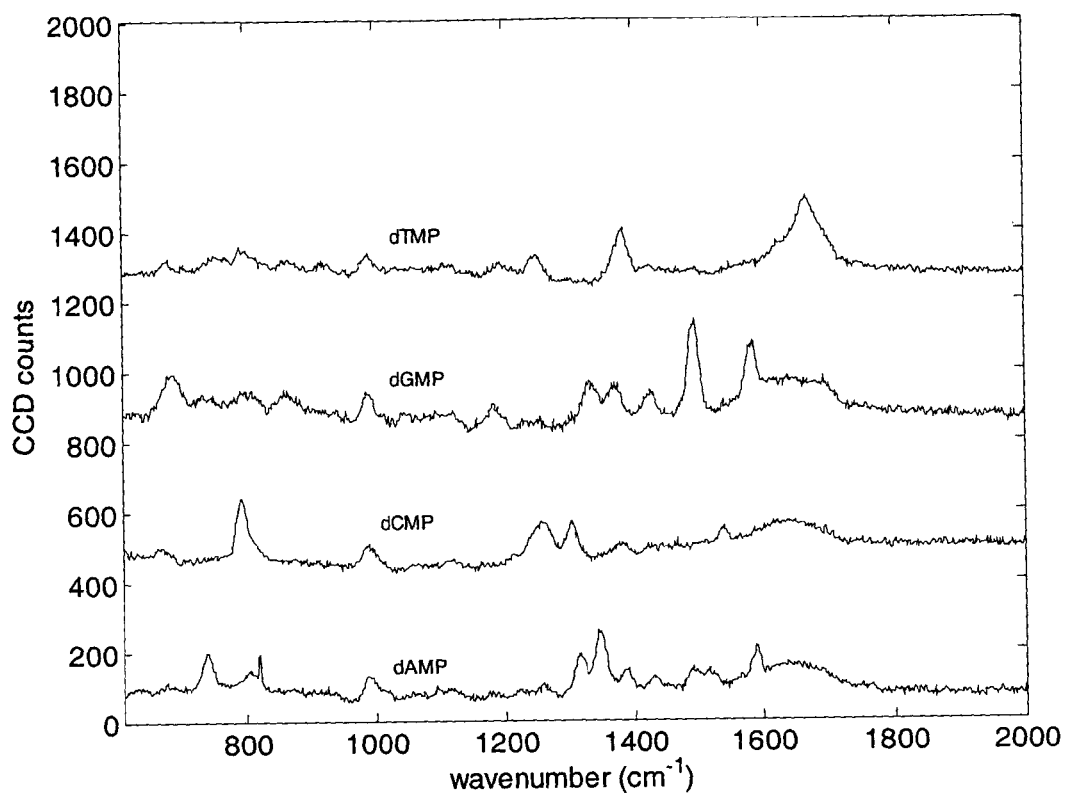
FIG. 8 shows the Raman spectra of four different types of nucleotides. Characteristic Raman emission peaks for each different type of nucleotide. The data were collected without surface-enhancement or labeling of the nucleotides.

Conditions were optimized for adenine nucleotides only. LiCl (90 µM final concentration) was determined to provide optimal SERS detection of adenine nucleotides. Detection of other nucleotides may be facilitated by use of other alkali-metal halide salts, such as NaCl, KCl, RbCl or CsCl. The claimed methods are not limited by the electrolyte solution used, and it is contemplated that other types of electrolyte solutions, such as MgCl, CaCl, NaF, KBr, LiI, etc. may be of use. The skilled artisan will realize that electrolyte solutions that do not exhibit strong Raman signals will provide minimal interference with SERS detection of nucleotides. The results demonstrate that the Raman detection system and methods disclosed above were capable of detecting and identifying single molecules of analyte FIG. 8 shows the Raman emission spectra of a 100 mM solution of four different types of nucleotides, in the absence of surface enhancement and without Raman labels. No LiCl was added to the solution. A 10 second data collection time was used. Excitation occurred at 514 nm. Lower concentrations of nucleotides may be detected with longer collection times, added electrolytes and/or surface enhancement. As shown in FIG. 8, the unenhanced Raman spectra showed characteristic emission peaks for each of the four unlabeled nucleoside monophosphates.

Surface-enhanced Raman emission spectra were obtained for a 1 nM solution of guanine, a 100 nM solution of cytosine, and a 100 nM solution of thymine in the presence of LiCl and silver nanoparticles (not shown). A 785 nm excitation wavelength was used. Each spectrum exhibited distinguishable Raman emission peaks (not shown).

Figure 9:
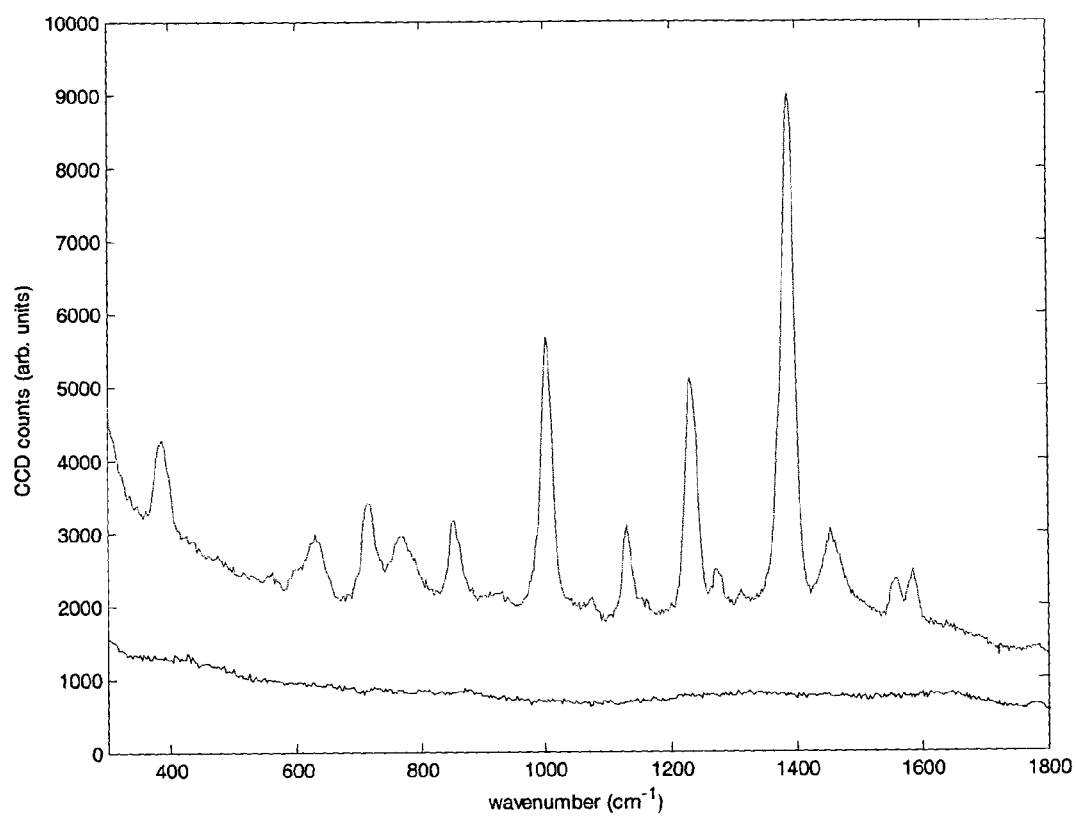
FIG. 9 shows a comparative SERS spectrum of a 500 nM solution of deoxyadenosine triphosphate covalently labeled with fluorescein (upper trace) and unlabeled dATP (lower trace). The dATP-fluorescein was obtained from Roche Applied Science (Indianapolis, Ind.). A strong increase in the SERS signal was detected for the fluorescein labeled dATP.

FIG. 9 shows the SERS spectrum of a 500 nM solution of dATP (lower trace) and fluorescein-labeled dATP (upper trace), with excitation at 785 nm. dATP-fluorescein was purchased from Roche Applied Science (Indianapolis, Ind.). The Figure shows a strong increase in SERS signal upon labeling with fluorescein.

An RCA product was detectable by SERS, with emission peaks at about 833 and 877 nm (not shown). Under the conditions of this protocol, with an LiCl enhancer, the signal strength from the adenine moieties was stronger than those for guanine, cytosine and thymine. The negative control (not shown) showed that the Raman signal was specific for the RCA product, as no signal was observed in the absence of amplification.

The skilled artisan will realize that the disclosed methods are exemplary only and that the Raman detection techniques disclosed for analysis of nucleotides and oligonucleotides are also applicable for amino acids and proteins. Using the disclosed techniques, specific types of amino acid residues on proteins may be covalently labeled, for example with a Raman tag. The labeled protein may be passed through a nanopore and the tagged residues detected, for example by Raman spectroscopy. As disclosed above, Raman spectroscopy may be used to detected tagged or untagged residues at the single molecule level. Detection of tagged amino acid residues may be used to construct distances maps, to identify and/or sequence proteins or other analytes of interest.

Example 6

Raman Detection of Amino Acids, Proteins and Peptides

Figure 10:
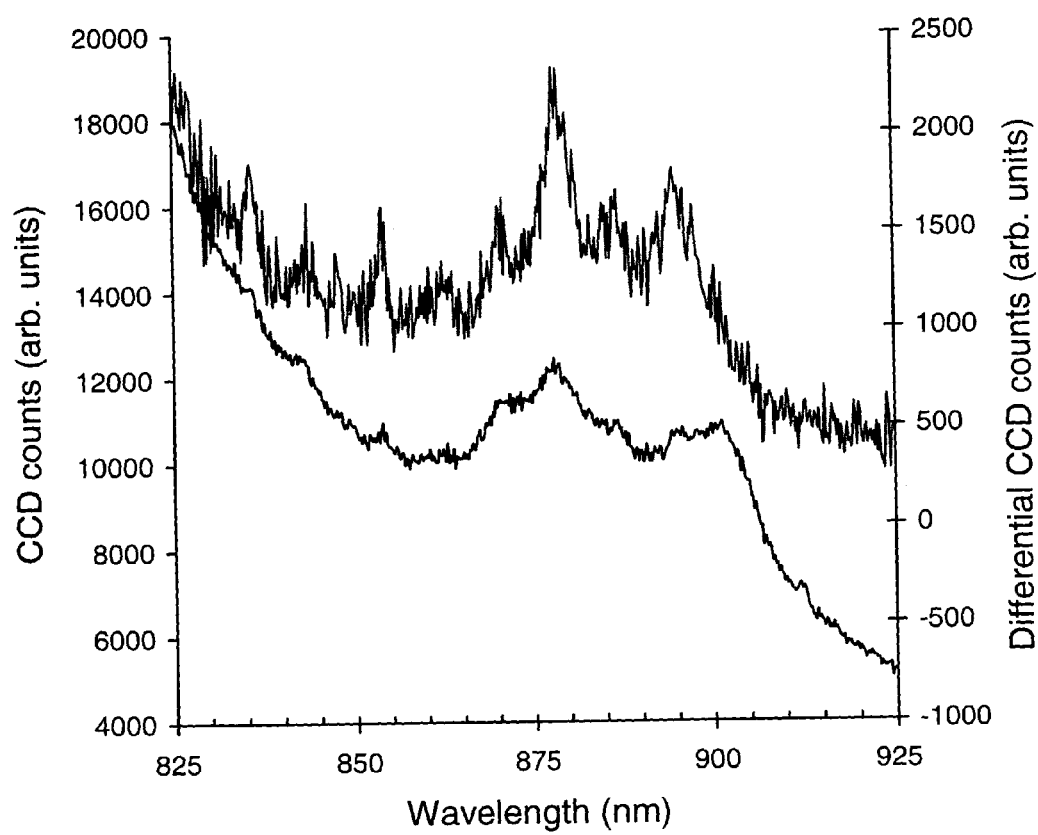
FIG. 10 illustrates the Raman spectrum of 1 mM tryptophan, taken with a 1 second (upper trace) and 0.1 second (lower trace) collection time.
Figure 11:
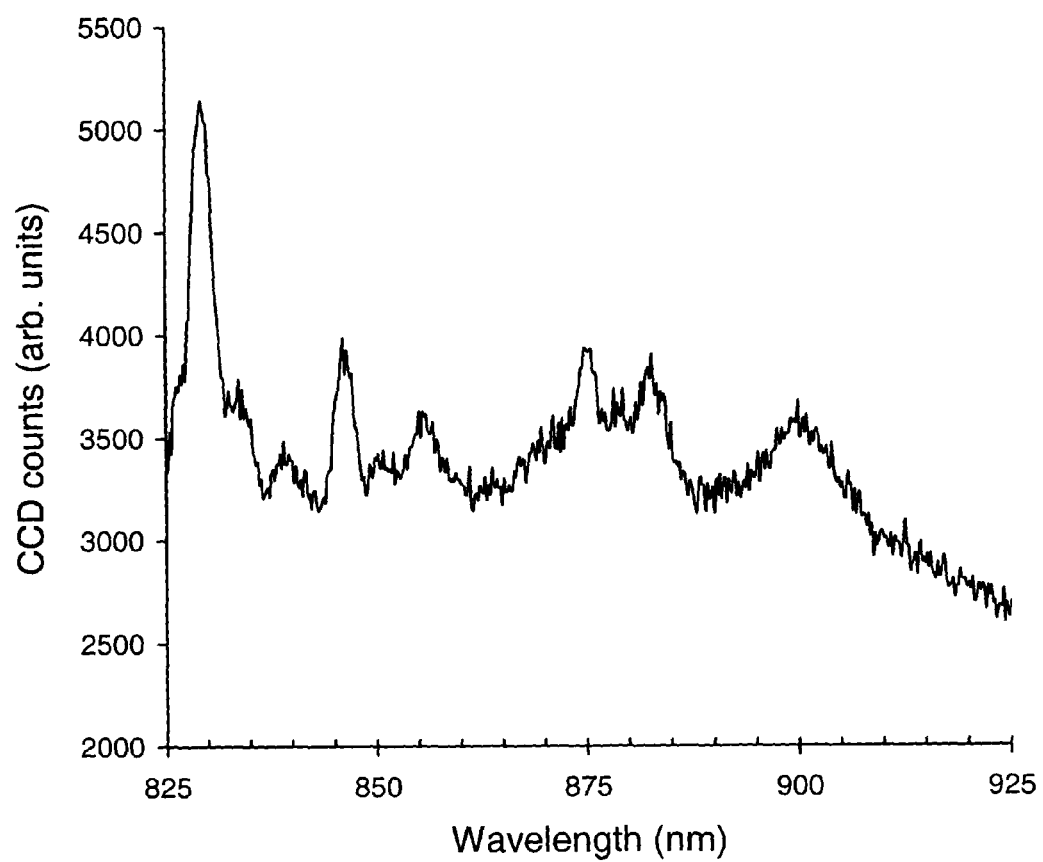
FIG. 11 shows the Raman spectrum of 1 mM cysteine, with a 0.1 second collection time.
Figure 12:
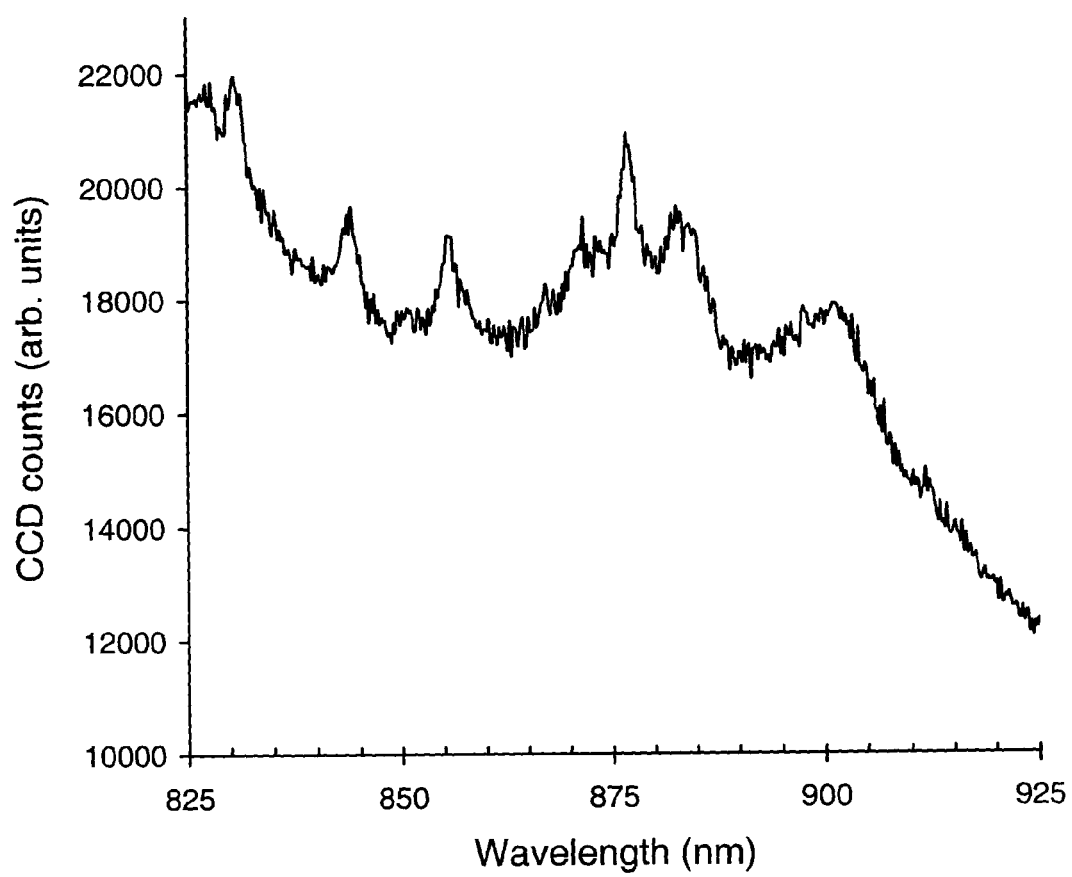
FIG. 12 exemplifies the Raman spectrum of 1 mM methionine, with a 1 second collection time.
Figure 13:
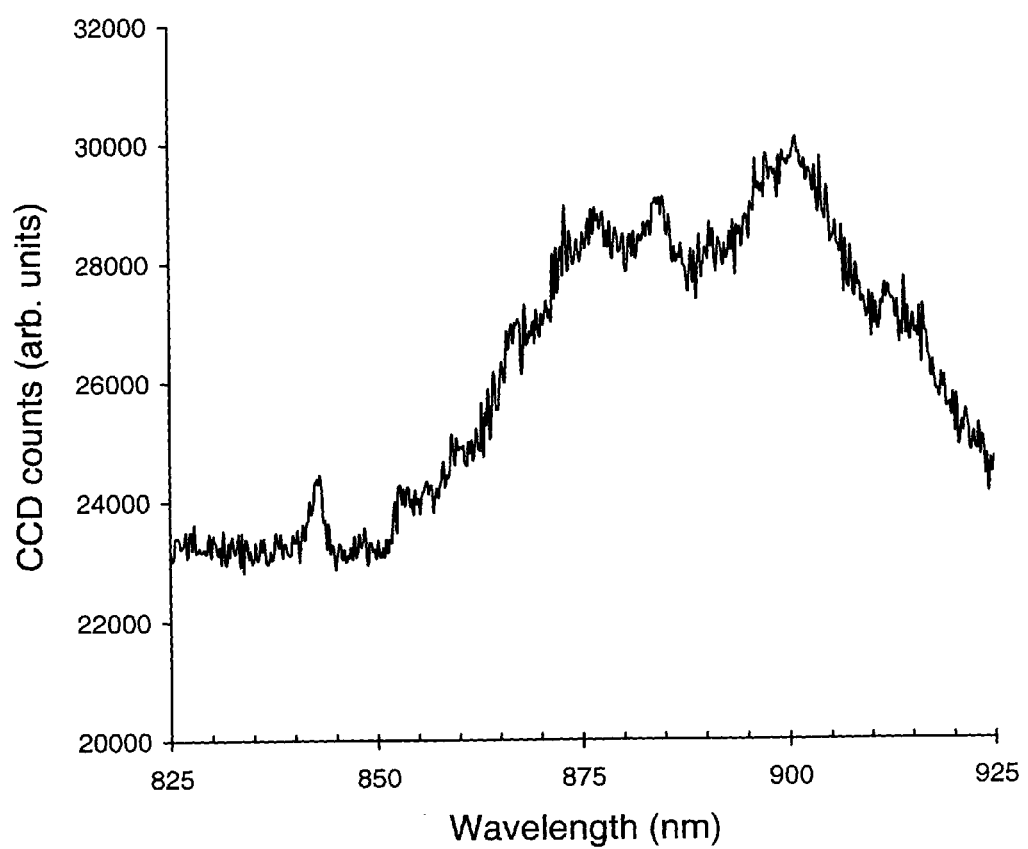
FIG. 13 illustrates the Raman spectrum of 1 mM histidine, with a 1 second collection time.
Figure 14:
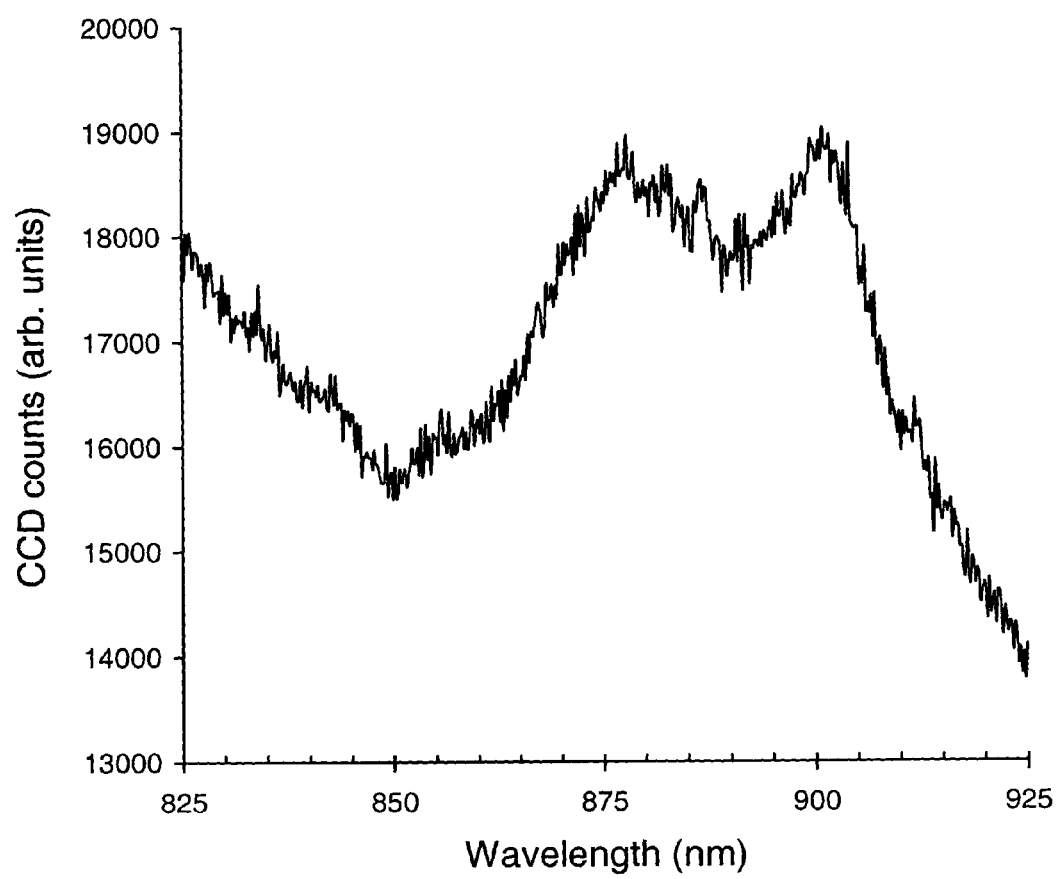
FIG. 14 shows the Raman spectrum of 1 mM phenylalanine, with a 1 second collection time.
Figure 15:
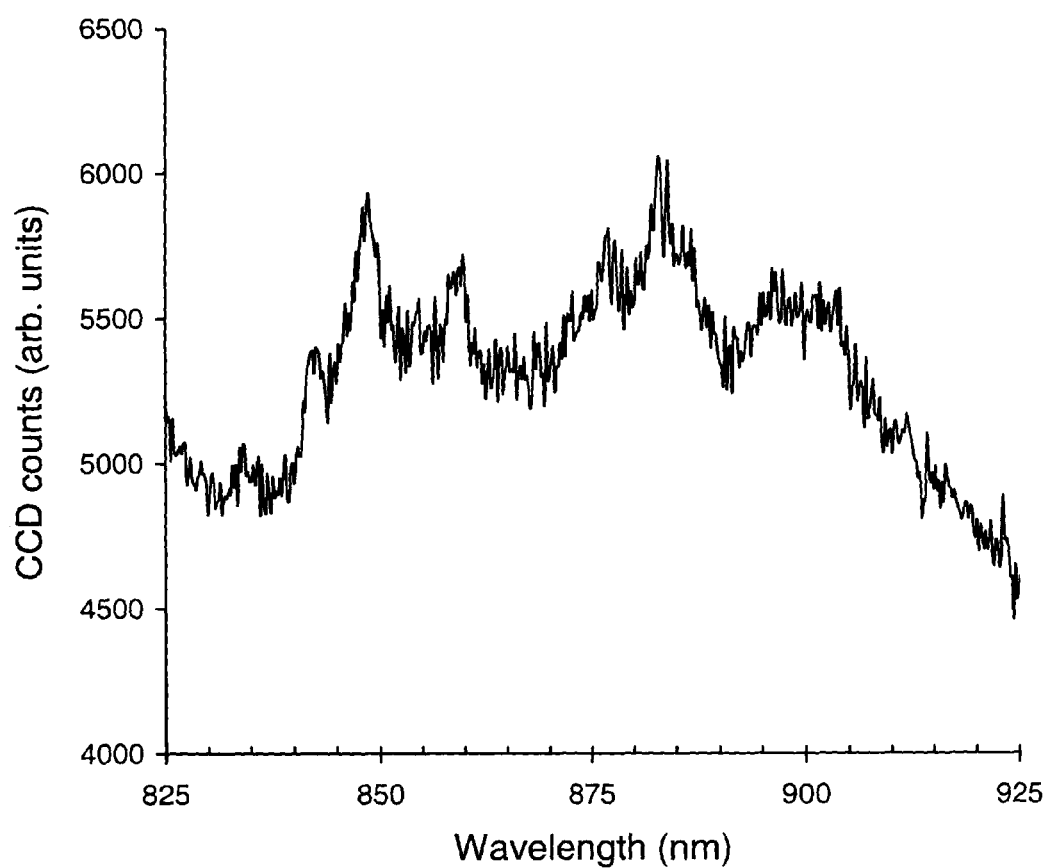
FIG. 15 shows the Raman spectrum of 1 mM arginine, with a 0.1 second collection time.
Figure 16:
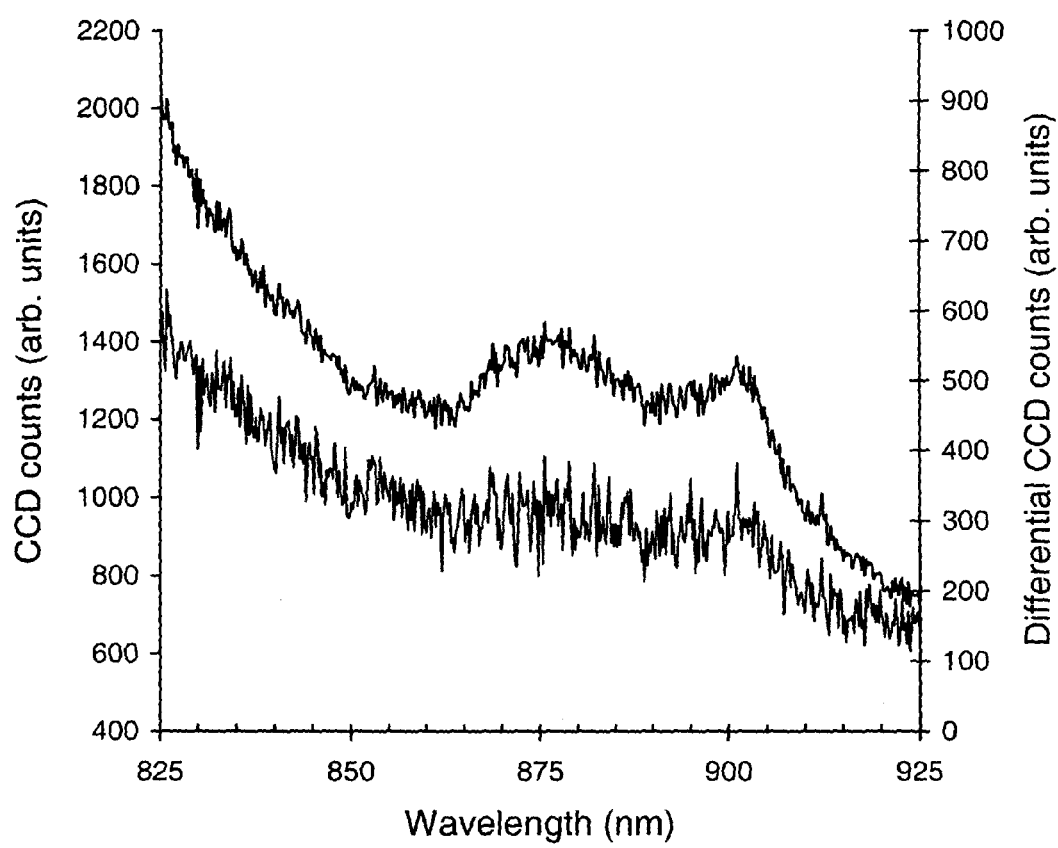
FIG. 16 shows the Raman spectrum of 1 mM tyrosine, with a 1 second collection time (upper trace) and 0.1 second collection time (lower trace).
Figure 17:
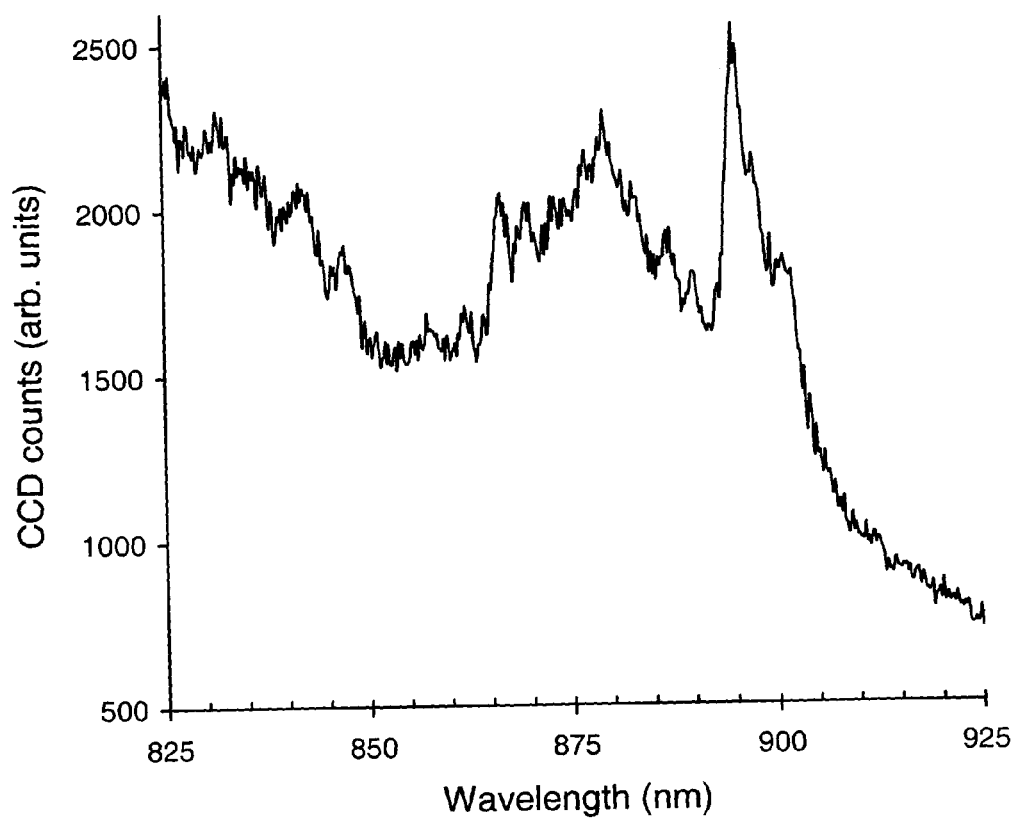
FIG. 17 shows the Raman spectra of 1 mM 5-fluorotryptophan, with a 0.1 second collection time.

Raman spectroscopy of amino acids, proteins and peptides was performed as disclosed in Example 5. As shown in FIG. 10 through FIG. 17, the SERS spectra of tryptophan, cysteine, methionine, histidine, phenylalanine, arginine and tyrosine all showed distinguishable SERS spectra, with characteristic Raman emission peaks. Derivatization of the amino acids also resulted in changes in the Raman spectra (compare FIG. 10 versus FIG. 17 for the SERS spectra of 1 mM tryptophan versus 5-fluorotryptophan). Attachment of a fluorine residue resulted in a considerable change in the SERS spectrum of tryptophan (FIG. 10 and FIG. 17). The spectrum was also dependent upon the position at which the fluorine residue was attached, with 5-fluorotryptophan (Sigma Chemicals, St. Louis, Mo.) giving a different SERS spectrum from 6-fluorotryptophan (not shown).

As discussed in the proceeding Example, it is concluded that Raman spectroscopic techniques, such as SERS, may be used to identify and distinguish different types of amino acid residues. The SERS spectra shown in FIG. 10 through FIG. 16 were obtained for unlabeled amino acids. As shown in FIG. 9 for nucleotide residues, covalent modification with a Raman label may produce a large increase in signal strength for the derivatized residue. As discussed above, side-chain specific labeling may be used to attach different types of Raman tags to different types of amino acid residues.

Figure 18:
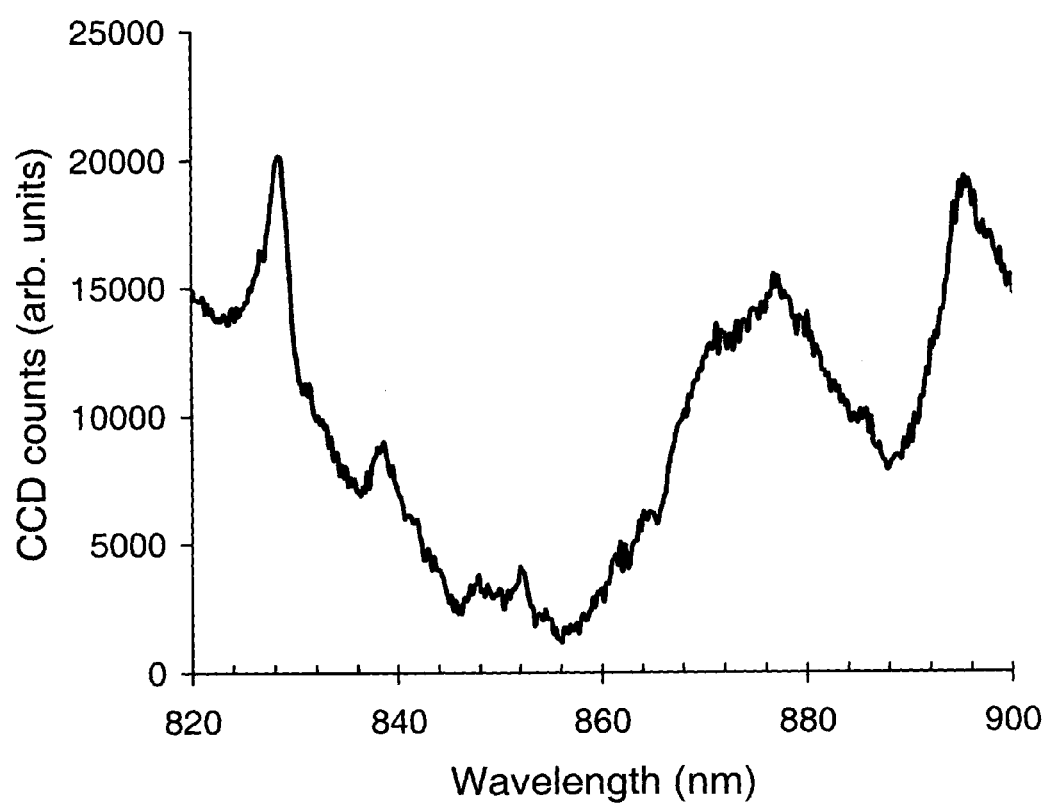
FIG. 18 illustrates the Raman spectrum of 1% fetal calf serum, dried on an aluminum plate, with a 1 second collection time.
Figure 19:
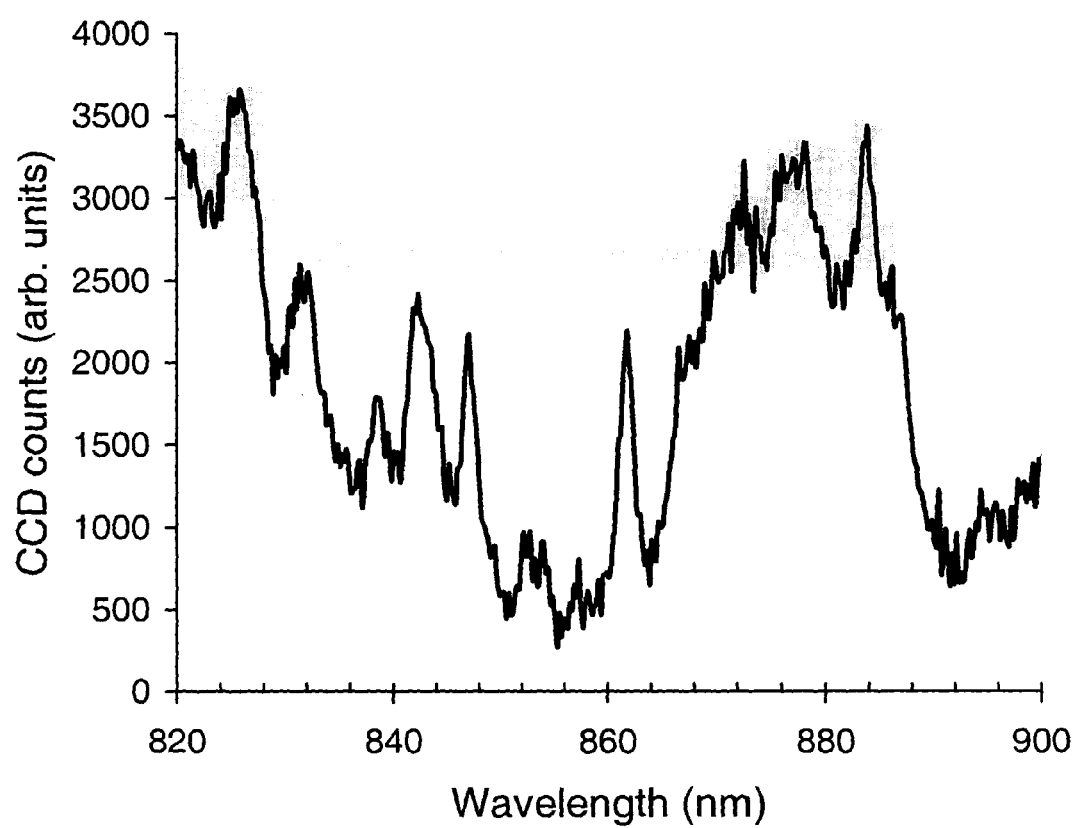
FIG. 19 shows the Raman spectrum of 100% whole calf serum, with a 1 second collection time.
Figure 20:
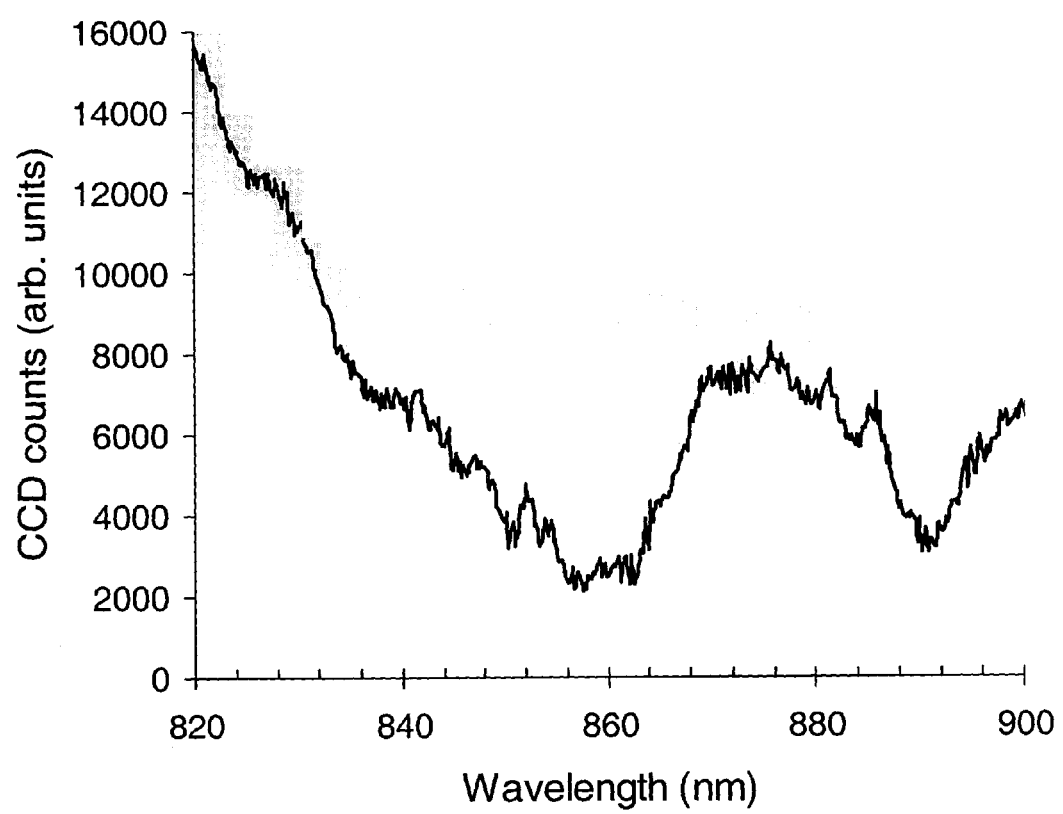
FIG. 20 shows the Raman spectrum of 0.1% whole calf serum, with a 1 second collection time.

SERS spectra were also obtained for whole proteins. FIG. 18 shows an exemplary SERS spectrum for 1% calf serum dried on an aluminum plate. Emission peaks were observed at 829, 839, 848, 852, 865, 872, 877, 886 and 896 nm. The SERS spectrum of 1% bovine serum albumin was similar, with slight differences observed in the spectrum (not shown). SERS detection of whole calf serum resulted in detection of characteristic peaks down to 0.1% serum (FIG. 19 and FIG. 20). FIG. 19 shows the SERS spectrum of 100% whole calf serum. A 160 µl aliquot of silver nanoparticles (diluted 1:2 with distilled water) was mixed with 20 µl of calf serum and 40 µl of 0.5 M LiCl. A 1 second collection time resulted in the spectrum shown in FIG. 19. The SERS spectrum showed emission peaks at 826, 832, 839, 842, 848, 854, 862, 873, 876 and 886 nm. A sample of 0.1% calf serum still resulted in a detectable SERS spectrum (FIG. 20), with detectable peaks at 842, 848, 854, 876, 882 and 886 nm.

Figure 21:
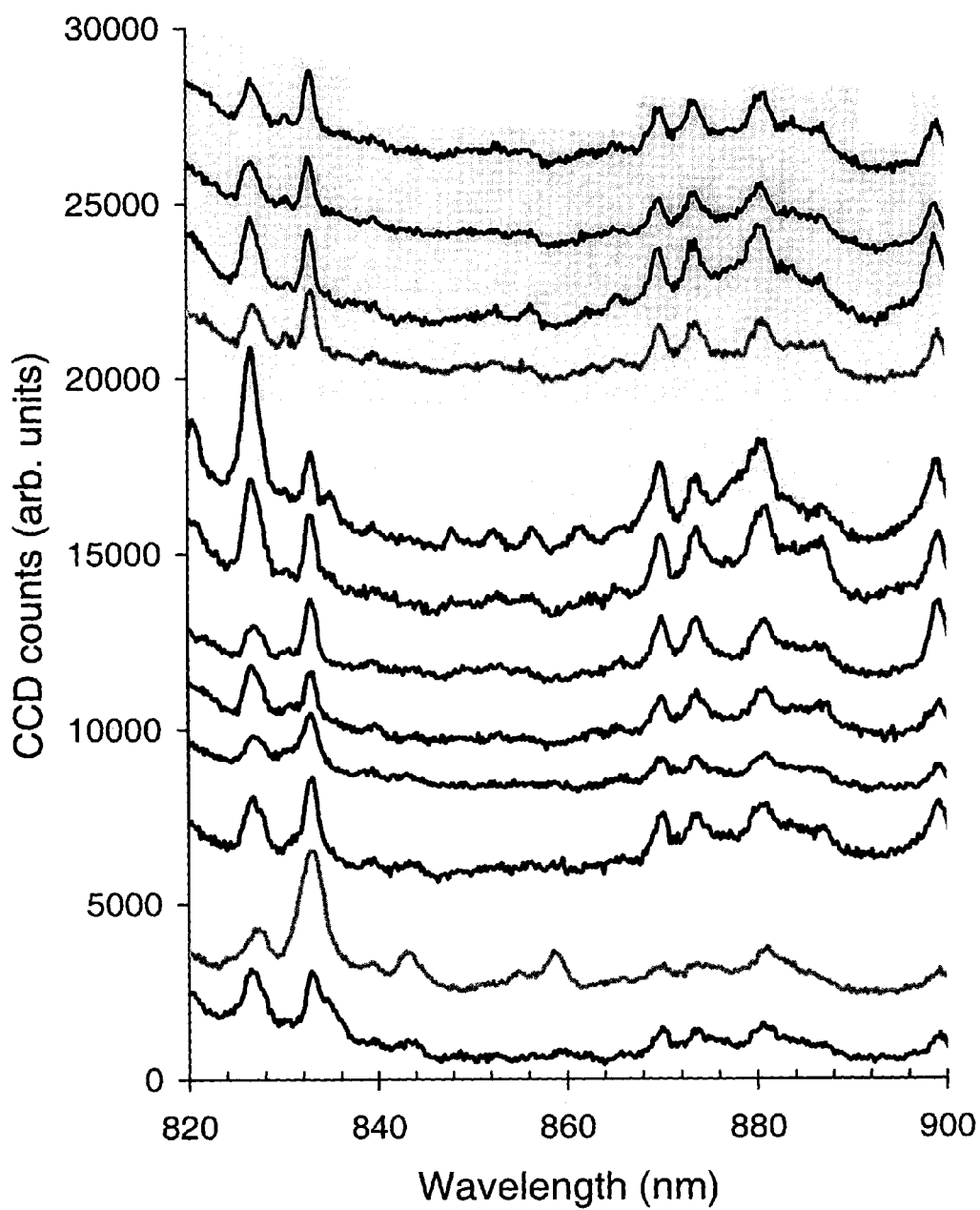
FIG. 21 shows the Raman spectra of various fragments obtained by trypsin digestion of serum protein. Peptides were separated by reverse-phase high pressure liquid chromatography (HPLC) on a C18 column.

SERS spectra were also obtained for a series of peptides, generated by trypsin digestion of serum proteins. The digested peptides were separated by reverse-phase HPLC on a C18 column. Elution of peptides occurred in an acidic mixture of trifluoroacetate and acetonitrile. The resulting peptides were analyzed by SERS spectroscopy (FIG. 21). It can be seen that different peptides showed distinguishable SERS spectra, with different sized peaks occurring at 827, 833, 844, 848, 853, 857, 859, 862, 870, 874 and 880 nm.

The results obtained demonstrate that SERS spectroscopy may be used to identify and distinguish different types of amino acid residues within proteins or peptides, allowing the production of distance maps for proteins detection, identification and/or sequencing.

All of the METHODS and APPARATUS disclosed and claimed herein can be made and executed without undue experimentation in light of the present disclosure. It will be apparent to those of skill in the art that variations may be applied to the METHODS and APPARATUS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

What is claimed is:

1. A method comprising:
   a) placing a plurality of labeled proteins, polypeptides or peptides in a plurality of chambers, such that different chambers contain a different type of labeled amino acid;
   b) passing the labeled proteins, polypeptides or peptides through one or more nanopores, an inner surface of the nanopores coated with a semiconductor material;
   c) detecting labeled amino acid residues in the labeled proteins, polypeptides or peptides;
   d) compiling an amino acid distance map for each type of labeled amino acid; and
   e) identifying the protein based on the distance maps.

2. The method of claim 1, further comprising:
   a) placing a template nucleic acid into each chamber; and
   b) producing the one or more labeled proteins, polypeptides or peptides encoded by the template nucleic acid.

3. The method of claim 1, further comprising: a) obtaining one or more proteins, polypeptides or peptides from a biological sample; and b) labeling the proteins, polypeptides or peptides post-translationally.

4. The method of claim 1, wherein the protein, polypeptide or peptide is identified by comparing the distance maps with a library of amino acid distance maps.

5. The method of claim 1, wherein the protein, polypeptide or peptide is identified by comparing the distance maps with the sequences of known proteins.

6. The method of claim 2, wherein each chamber is operably coupled to a different set of nanopores.

7. The method of claim 1, wherein each nanopore is operably coupled to a detector.

8. The method of claim 1, wherein only one labeled protein, polypeptide or peptide passes through a nanopore at a time.

9. The method of claim 1, wherein the length of time between passage of a first labeled amino acid through the nanopore and passage of a second labeled amino acid through the nanopore corresponds to the distance along the labeled protein, polypeptide or peptide between the first and second amino acids.

10. The method of claim 1, wherein the labels are selected from the group consisting of luminescent labels, fluorescent labels, phosphorescent labels, chemiluminescent labels, conductive labels, nuclear magnetic resonance labels, mass spectroscopy labels, electron spin resonance labels, electron paramagnetic resonance labels and Raman labels.

11. The method of claim 1, wherein at least one end of the labeled protein, polypeptide or peptide is attached to an identifiable label.

12. The method of claim 1, wherein said labeled amino acids are detected with a photodetector.

13. The method of claim 1, wherein said labeled amino acids are detected with an electrical detector.

14. The method of claim 2, further comprising analyzing a multiplicity of labeled proteins, polypeptides or peptides from each chamber.

15. The method of claim 1, further comprising determining at least a partial sequence of the protein, polypeptide or peptide based on the distance maps.

16. The method of claim 2, wherein the one or more labeled proteins, polypeptides or peptides encoded by the template nucleic acid is produced by in vitro translation or by linked transcription/translation.

17. The method of claim 16, wherein in vitro translation is performed with mRNA templates.

18. The method of claim 16, wherein in vitro translation carried out in cell systems of rabbit reticulocyte lysates, wheat germ extracts, or *E. coli* extracts.

19. The method of claim 1, wherein the distance map shows distances in a sub-nanometer scale.

* * * * *